US009581598B2

(12) United States Patent
Ruoslahti et al.

(10) Patent No.: US 9,581,598 B2
(45) Date of Patent: Feb. 28, 2017

(54) DIAGNOSIS AND TREATMENT OF BRAIN TUMOR

(71) Applicant: Sanford-Burnham Medical Research Institute, La Jolla, CA (US)

(72) Inventors: Erkki Ruoslahti, Buellton, CA (US); Pirjo Laakkonen, Helsinki (FI)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 14/396,414

(22) PCT Filed: Apr. 25, 2013

(86) PCT No.: PCT/US2013/038219
§ 371 (c)(1),
(2) Date: Oct. 23, 2014

(87) PCT Pub. No.: WO2013/163431
PCT Pub. Date: Oct. 31, 2013

(65) Prior Publication Data
US 2015/0212086 A1    Jul. 30, 2015

Related U.S. Application Data

(60) Provisional application No. 61/638,064, filed on Apr. 25, 2012.

(51) Int. Cl.
| | |
|---|---|
| *A61K 6/00* | (2006.01) |
| *A61K 31/00* | (2006.01) |
| *A61K 31/16* | (2006.01) |
| *A61K 31/70* | (2006.01) |
| *A61K 31/7042* | (2006.01) |
| *A61K 31/7052* | (2006.01) |
| *A61K 31/706* | (2006.01) |
| *G01N 33/574* | (2006.01) |
| *A61K 31/713* | (2006.01) |
| *A61K 39/395* | (2006.01) |
| *A61K 45/06* | (2006.01) |
| *C07K 16/18* | (2006.01) |
| *C12N 15/113* | (2010.01) |

(52) U.S. Cl.
CPC ..... *G01N 33/57407* (2013.01); *A61K 31/713* (2013.01); *A61K 39/39558* (2013.01); *A61K 45/06* (2013.01); *C07K 16/18* (2013.01); *C12N 15/113* (2013.01); *C12N 2310/14* (2013.01); *C12N 2310/531* (2013.01); *G01N 2333/4704* (2013.01); *G01N 2800/52* (2013.01); *G01N 2800/56* (2013.01)

(58) Field of Classification Search
CPC .......... A61K 6/00; A61K 31/00; A61K 31/16; A61K 31/70; A61K 31/7042; A61K 31/7052; A61K 31/706; A61K 2121/00; A61K 2300/00; C12Q 2304/00; C12Q 2522/00; C12Q 2522/10; C12Q 2522/101; C12Q 2537/00; C12Q 2537/10; C12Q 2537/137; C12Q 2537/164
See application file for complete search history.

(56) References Cited

U.S. PATENT DOCUMENTS

2002/0127619 A1   9/2002   Jett

FOREIGN PATENT DOCUMENTS

EP   1669451   6/2006

OTHER PUBLICATIONS

Calias et al. (Pharmacology & Therapeutics 144: 114-122, 2014).*
Chandramohan et al. Future Oncology 9(7): 977-990, Jul. 2013.*
Blouw, et al., "The hypoxic response of tumors is dependent on their microenvironment", Cancer Cell, 4:133-46 (2003).
Borkhardt, "Blocking oncogenes in malignant cells by RNA interference—new hope for a highly specific cancer treatment", Cancer Cell, 2:167-8 (2002).
Dykxhoorn, et al., "The silent revolution: RNA interference as basic biology, research tool, and therapeutic", Annu. Rev. Med., 56:401-23 (2005).
Gilmore, et al., "The design and exogenous delivery of siRNA for post-transcriptional gene silencing", J. Drug Target., 12(6):315-40 (2004).
Glatz and Van Der Vusse, "Cellular fatty acid-binding proteins: their function and physiological significance", Prog Lipid Res., 35:243-82 (1996).
Goto, et al., "Circulating concentrations of cardiac proteins indicate the severity of congestive heart failure", Heart, 89(11):1303-7 (2003).
Hannon, "RNA interference", Nature, 418:244-51 (2002).
Hashimoto, et al., "Expression of heart-type fatty acid-binding protein in human gastric carcinoma and its association with tumor aggressiveness, metastasis and poor prognosis", Pathobiology, 71:267-73 (2004).
Huynh and Pollak, "HH2A, an immortalized bovine mammary epithelial cell line, expresses the gene encoding mammary derived growth inhibitor (MDGI).", In Vitro Cell Dev Biol Anim., 31:25-9 (1995).
Huynh, et al., "Silencing of the mammary-derived growth inhibitor (MDGI) gene in breast neoplasms is associated with epigenetic changes", Cancer Res., 56:4865-70 (1996).
Jiang, et al., "Gel-based application of siRNA to human epithelial cancer cells induces RNAi-dependent apoptosis", Oligonucleotides, 14(4):239-48 (2004).
Laakkonen, et al., "A tumor-homing peptide with a targeting specificity related to lymphatic vessels", Nat Med., 8:751-5 (2002).
Lewis, et al., "Efficient delivery of siRNA for inhibition of gene expression in postnatal mice", Nat Genet., 32:107-8 (2002).
McManus, et al., "Gene silencing in mammals by small interfering RNAs", Nat Rev Genet., 3:737-47 (2002).

(Continued)

*Primary Examiner* — Alana Harris Dent
(74) *Attorney, Agent, or Firm* — Pabst Patent Group LLP

(57) ABSTRACT

Cellular targets on cancer cells have been identified that can be used with targeted molecular imaging to detect the cancer cells in vivo. Non-invasive methods for detecting cancer cells, such as metastasized cancer cells, are therefore provided. Also provided are compositions and kits for use in the disclosed methods.

7 Claims, 5 Drawing Sheets

(56) References Cited

OTHER PUBLICATIONS

Nevo, et al., "Mammary-derived growth inhibitor (MDGI) interacts with integrin a-subunits and suppresses integrin activity and invasion", Oncogene, 29 (49):6452-63 (2010a).
Nevo, et al., "Mammary-derived growth inhibitor alters traffic of EGFR and induces a novel form of cetuximab resistance", Clin Cancer Res., 15:6570-81 (2009).
Nevo, "Novel players in the integrin signaling orchestra: TCPTP and MDGI", Turun Yliopisto University of Turku, Turku, pp. 46-52 (2010b).
Paul, et al., "Effective expression of small interfering RNA in human cells", Nat Biotechnol., 20:505-8 (2002).
Pelsers, et al., "Brain- and heart-type fatty acid-binding proteins in the brain: tissue distribution and clinical utility", Clinical Chemistry, 50(9):1568-75 (2004).
Porkka, et al., "A fragment of the HMGN2 protein homes to the nuclei of tumor cells and tumor endothelial cells in vivo", PNAS., 99:7444-9 (2002).
Sarkar, et al., "Condensation of oligonucleotides assembled into nicked and gapped duplexes: potential structures for oligonucleotide delivery", Nucleic Acids Research, 33(1):143-51 (2005).
Scherr, et al., "Gene silencing mediated by small interfering RNAs in mammalian cells", Curr Med. Chem., 10:245-56 (2003).
Setsuta, et al., "Use of cytosolic and myofibril markers in the detection of ongoing myocardial damage in patients with chronic heart failure", Am J. Med., 113:717-22 (2002).
Shuey, et al., "RNAi: gene-silencing in therapeutic intervention", Drug Discov Today, 7:1040-6 (2002).
Song, et al., "RNA interference targeting Fas protects mice from fulminant hepatitis", Nat Med., 9:347-51 (2003).
Sorensen, et al., "Gene silencing by systemic delivery of synthetic siRNAs in adult mice.", J Mol Biol., 327:761-6 (2003).
Storch and Corsico, "The emerging functions and mechanisms of mammalian fatty acid-binding proteins", Annu. Rev. Nutr., 28:73-95 (2008).
Tanaka, et al., "Serum and urinary human heart fatty acid-binding protein in acute myocardial infarction", Clin Biochem, 24:195-201 (1991).
Veerkamp, "Fatty acid transport and fatty acid-binding proteins", Proc Nutr Soc., 54:23-37 (1995).
Wang and Kurtz, "Breast cancer growth inhibition by delivery of the MDGI-derived derived peptide P108", Oncogene 19(20):2455-60 (2000).
Yang, et al., "Members of the fatty acid binding protein family are differentiation factors for the mammary gland", J. Cell Biol., 127:1097-1109 (1994).
Zhang, et al., "Suppression subtractive hybridization to identify gene expressions in variant and classic small cell lung cancer cell lines", J. Surg. Res., 93 (1):108-19 (2000).
Zimmermann, et al., "RNAi-mediated gene silencing in non-human primates", Nature, 441:111-4 (2006).

* cited by examiner

SEQUENCE LISTING

<160> NUMBER OF SEQ ID NOS: 8

<210> SEQ ID NO 1

-continued

```
<211> LENGTH: 33
<212> TYPE: DNA
<213> ORGANISM: Artificial Sequence
<220> FEATURE:
<223> OTHER INFORMATION: Synthetic Primer

<400> SEQUENCE: 1
aattctgcgg actgagcggg ttaggcgttg ctg                              33

<210> SEQ ID NO 2
<211> LENGTH: 33
<212> TYPE: DNA
<213> ORGANISM: Artificial Sequence
<220> FEATURE:
<223> OTHER INFORMATION: Synthetic Primer

<400> SEQUENCE: 2
gatccagcaa cgcctaaccc gctcagtccg cag                              33

<210> SEQ ID NO 3
<211> LENGTH: 34
<212> TYPE: DNA
<213> ORGANISM: Artificial Sequence
<220> FEATURE:
<223> OTHER INFORMATION: Synthetic Primer

<400> SEQUENCE: 3
ggaattcgcg gacgcctttg tcggtacctg gaag                             34

<210> SEQ ID NO 4
<211> LENGTH: 38
<212> TYPE: DNA
<213> ORGANISM: Artificial Sequence
<220> FEATURE:
<223> OTHER INFORMATION: Synthetic Primer

<400> SEQUENCE: 4
cctcgagtca cgcctccttc tcataagtcc gagtgctc                         38

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Cys Gly Leu Ser Gly Leu Gly Val Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 6

Cys Ser Glu Ser Gly Leu Gly Val Ala
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (1)..(1)
<223> OTHER INFORMATION: NH2 modification
<220> FEATURE:
<221> NAME/KEY: MISC_FEATURE
<222> LOCATION: (10)..(10)
<223> OTHER INFORMATION: CONH2 modification

<400> SEQUENCE: 7

Ala Cys Val Ala Ala Leu Asn Ala Asp Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: NH2 modification
<220> FEATURE:
<221> NAME/KEY: MISC_FEATURE
<222> LOCATION: (10)..(10)
<223> OTHER INFORMATION: CONH2 modification

<400> SEQUENCE: 8

Ala Cys Gly Leu Ser Gly Leu Gly Val Ala
1               5                   10
```

DIAGNOSIS AND TREATMENT OF BRAIN TUMOR

CROSS REFERENCE TO RELATED APPLICATIONS

This application is a 371 application of International Application No. PCT/US2013/038219, filed Apr. 25, 2013, which claims the benefit of and priority to U.S. Provisional Application No. 61/638,064, filed Apr. 25, 2012.

FIELD OF THE INVENTION

The disclosed invention is generally in the field of diagnosing brain tumor in a subject and specifically in the area of using antibodies to diagnose brain tumor/deliver therapeutic agents to brain tumors.

REFERENCE TO SEQUENCE LISTING

The Sequence Listing submitted Mar. 4, 2015, as a text file named SBMRI_12_056_ST25.txt," created on Jan. 15, 2015, and having a size of 2,127 bytes is hereby incorporated by reference pursuant to 37 C.F.R. §1.52(e)(5).

BACKGROUND OF THE INVENTION

The brain consists of two types of cells: neurons and glial cells. Neurons are the cells that receive and send messages within the brain and make up what is referred to as gray matter (composed of cell bodies) and white matter (composed of axons). Glial cells are non-neuronal cells that provide support and protection for neurons. Astrocytes are a sub-type of glial cells in the brain and spinal cord. They retain their capacity for division throughout their life span, which makes them susceptible for transformation and contribute to the prevalence of astrocyte-derived tumors.

Brain tumors are caused by an abnormal and uncontrolled cell growth in the brain itself or as metastatic lesions of tumors in other organs. Low-grade astrocytomas, a class of malignant brain tumors, acquire their blood supply by co-opting existing normal blood vessels and propagating along them without initiating angiogenesis. This leads to diffuse invasion of tumor cells over long distances in the brain without formation of real tumor masses. As grade III astrocytomas progress to grade IV astrocytomas they grow in size, and to cope with the increased need for nutrients and oxygen they undergo an angiogenic switch. Glioblastoma multiforme (GBM) are the most malignant form of astrocytomas. They become highly vascularized and tumors appear more local than the low-grade astrocytomas. GBMs also retain the ability of invasive growth.

With respect to therapy, brain tumors that are beyond the reach of conventional therapies (e.g., surgery or radiation) and which grow diffusively to invade the brain are especially challenging to treat.

Inhibition of tumor angiogenesis is a therapeutic strategy, which has been used to treat a variety of malignant tumors. Systemic anti-angiogenic treatment of malignant brain tumors has shown to increase the number of satellite tumors in experimental animal models. There are reports according to which the treatment might even encourage tumor cells to more invasive phenotype.

WO 2009/136007 describes a peptide, CooP, which specifically homes to intracranial, early stage astrocytoma model that grows as islets and harbors co-opted tumor vessels in the brain. The peptide can be used in targeted delivery of therapeutic substances to invasive brain cancers or metastatic brain lesions and as a diagnostic tool.

However, new therapies for aggressive tumors are still needed and also new methods to recognize the most aggressive tumors from the less aggressive ones. Better diagnosis and treatment methods are needed, especially for invasive brain cancers and metastatic lesions of other tumor types in the brain.

It is an object of the present invention is to provide a method for determining the presence or grade of brain tumor in a patient.

It is a further object of the present invention to provide a method for treating brain tumor in a patient.

It is a further object of the present invention is to provide products, which can be used in diagnosis or treatment of brain tumors or metastatic lesions in the brain.

BRIEF SUMMARY OF THE INVENTION

Provided herein are compositions and methods for determining the presence and/or grade of brain tumor in a patient, such as invasive brain tumor. Also provided are methods for diagnosing and treating brain tumor or metastatic brain lesions or other tumor types.

The methods and compositions provided herein are based on the finding that mammary-derived growth inhibitor, MDGI (also known as fatty acid binding protein 3 (FABP-3) and heart type fatty acid binding protein (H-FAPB)), is the receptor/binding protein that the CooP peptide recognizes in the brain tumors (WO 2009/136007). The studies described herein show that MDGI is expressed in brain tumors and in particular in lesions typical for brain tumors which cannot be removed by surgery. The Examples show for the first time that MDGI expression becomes upregulated in brain tumors. Furthermore, MDGI is expressed on the vasculature of brain tumors. In other tissues (e.g., skeletal muscle, mammary fat pad, and heart) MDGI is not normally expressed on the vasculature. Based on these surprising findings, it was discovered that MDGI can be used for diagnosis and treatment of brain tumors. In addition, the examples described herein show that the increase of MDGI expression increases the invasion and metastasis of tumors. Therefore, by inhibiting MDGI expression or MDGI functions, the invasion and metastatic spread of cancer can be inhibited/reduced.

Accordingly, the methods provided herein for determining the presence or grade of brain tumor include, for example, determining the level of MDGI in a sample obtained from a subject, and comparing the level of MDGI in the sample with the level of MDGI in a control sample. The sample can be, for example, blood or fractions thereof, typically in plasma or serum, or tumor tissue sample obtained from a patient. A difference in the amount of MDGI in the sample relative to a control sample is indicative of the presence or grade of brain tumor. The level of MDGI can be determined by using anti-MDGI antibody or other molecule recognizing MDGI. In these forms the anti-MDGI antibody or other molecule recognizing MDGI can be labeled with a detectable label. The methods can include, for example, the steps of conjugating the anti-MDGI antibody to a detectable label, administering the labeled anti-MDGI antibody to the patient, and detecting the label.

Also provided herein are targeted therapies for treating brain tumors. The method includes targeting pharmaceutically active agents to brain tumor or metastatic brain lesions or other tumor types, using an anti-MDGI antibody or other molecule recognizing MDGI. In some forms, the methods of treating brain tumors can include inhibiting MDGI expression or function in the tumor or metastatic lesion by the aid of said antibody. In some forms, MDGI function can be inhibited by using a molecule that inhibits MDGI expression or function. In some forms, MDGI expression or function can be inhibited by using a nucleic acid molecule that inhibits MDGI gene expression. The methods for targeted therapy of invasive brain cancer or metastatic brain lesions, or other tumor types, can include administering to a patient in need of such therapy an effective amount of a pharmaceutical composition comprising, for example, anti-MDGI antibody or shRNA or siRNA for silencing MDGI expression or function. The methods of treatment disclosed herein can further include combining the targeted therapy with conventional cancer therapies selected from, for example, radiation and anti-cancer or anti-angiogenic therapies. In some forms, the method of targeted therapy disclosed herein can be combined with surgery.

Also provided is a method for monitoring the efficacy of brain cancer therapy or relapse following surgical removal of cancer. The method can include monitoring MDGI levels as described herein, whereby decreasing MDGI levels following removal of cancer are indicative of efficacy and increasing MDGI levels following removal of cancer is indicative of a relapse.

Also provided herein are molecules and compositions for use in inhibiting MDGI expression or function in the brain. In some forms, the molecules can be anti-MDGI antibodies. In some forms, the molecules can be nucleic acids; for example, shRNA or siRNA which inhibit MDGI expression in the brain tumor or metastatic lesion in brain. In some forms, compositions comprising anti-MDGI antibody, siRNA of shRNA are provided for use in treating brain tumor or metastatic lesions in the brain or other tumor types.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 2A shows CooP phage and unselected library binding to U20S cells transfected with MDGI (data is expressed as fold increase over the control phage±SEM.). FIG. 2B shows MDGI expression in the transfected cells confirmed by Western blot analysis using an antibody against MDGI and c-Myc.

DETAILED DESCRIPTION OF THE INVENTION

Figure 1A:
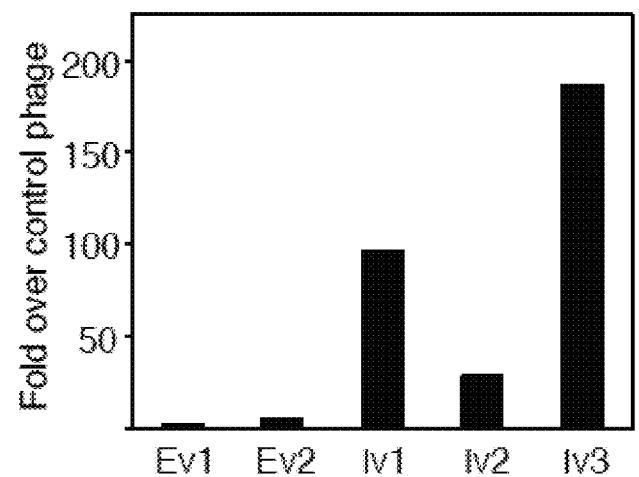
FIGS. 1A-1C are bar graphs of a phage screen of two ex vivo (Ev) rounds performed by incubating the phage with cell suspension from HIFko tumors followed by three in vivo (Iv) rounds with intravenously injected phage pool into intracranial HIFko astrocytoma-bearing mice. Phage enrichment is shown as fold increase over the control phage (FIG. 1A). Individual phage from the third in vivo selection round were tested for ex vivo binding to the cell suspension derived from tumor containing brain and normal brain. Graph shows phage binding to tumor brain relative to the normal brain (FIG. 1B). Specificity of the CooP phage homing to the brain tumors and histologically normal brain, liver, kidney and lung tissue compared to the control phage (FIG. 1C).

The disclosed methods and compositions may be understood more readily by reference to the following detailed description of particular embodiments and the Example included therein and to the Figures and their previous and following description.

Mammary-derived growth inhibitor (MDGI; also known as H-FABP and FABP-3) is a small 15-kDa cytosolic protein that belongs to the family of fatty acid-binding proteins (FABPs). Sequencing of the cDNA of MDGI has shown an open reading frame coding for a protein of 133 amino acids (Kurtz et al., *J. Cell Biol.*, 110(5):1779-89 (1990)). The sequence data is also available from EMBL/GenBank DDJB accession number X51933 or NM 004102. Expression of the fatty acid-binding proteins is relatively tissue specific. Fatty acid-binding proteins avidly bind hydrophobic ligands and mediate fatty acid metabolism (Hanhoff, et al., *Mol Cell Biochem*, 239:45-54 (2002)). MDGI is expressed at least in 39 different tissues, including the heart, brain, lung, and breast (Therry-Mieg, et al., Genome Biol., 7(Suppl 1):S12 1-4 (2006)). With respect to pathologies, MDGI is abundant in the myocardium and is released into circulation after myocardium injury. MDGI can be used as a sensitive early marker to detect the myocardial damage in diseases such as acute myocardial infarction and chronic heart failure (Tanaka et al., *Clin Biochem*, 24:195-201 (1991); Setsuta, et al., *Am J. Med.*, 113:717-722 (2002)). Moreover, MDGI is a valuable prognostic marker, since circulating concentrations of MDGI can indicate the severity of congestive heart failure (Goto et al., *Heart*, 89(11):1303-7 (2003)). MDGI has also been suggested as a circulating marker for the stroke (Pelsers et al. *Clinical Chemistry*, 50(9):1568-75 (2004)).

The examples described herein show that the anti-MDGI antibody accumulates in the tumor-associated vasculature after intravenous injection, whereas blood vessels in other tissues such as muscle, heart, normal brain, kidney, liver, and lung show no detectable accumulation of the antibody. The studies also show that in the tumor tissue, MDGI was accessible via the blood circulation, and could therefore act as a receptor molecule for intravenously administered antibodies or other molecules recognizing MDGI.

The disclosed method can take certain forms. For example, disclosed is a method for determining the presence or grade of brain tumor or metastatic brain lesions or other brain tumor types in a patient, comprising: (i) determining the level of MDGI in a sample obtained from a patient; (ii) comparing the level of MDGI in the sample with the level of MDGI in a control sample; wherein a difference in the amount of MDGI in the sample relative to the control sample is indicative of the presence or grade of brain tumor or other brain tumor type. As another example, disclosed is a method for targeted therapy of brain cancer or metastatic brain lesions, or other brain tumor types comprising administering to a patient in need of such therapy an efficient amount of a pharmaceutical composition comprising anti-MDGI antibody or siRNA or shRNA for MDGI. As another example, disclosed is a method for diagnosing brain tumor or metastatic brain lesion or other brain tumor types in a patient, comprising the steps of: conjugating an anti-MDGI antibody to a detectable label, administering the labeled anti-MDGI antibody to the patient, and detecting the label. As another example, disclosed is the use of the MDGI levels obtained in the disclosed methods for monitoring the efficacy of therapy or relapse after the surgical removal of the brain tumor or metastatic lesion or other type of tumor tissue in brain.

In some forms, the sample is selected from the group consisting whole blood, blood plasma, serum or tumor tissue. In some forms, the level of MDGI is determined by using anti-MDGI antibody or other molecule recognizing MDGI. In some forms, the anti-MDGI antibody or other molecule is labeled with a detectable label, such as an imaging agent. In some forms, the method further comprises combining the said targeted therapy with cancer therapies.

The disclosed compositions can also take certain forms. For example, disclosed is anti-MDGI antibody for use in diagnosing or treating brain tumor or metastatic brain lesions or other brain tumor types. As another example, disclosed is anti-MDGI antibody for use in targeting pharmaceutically active agents to brain tumor or metastatic brain lesions or other brain tumor types. As another example, disclosed is anti-MDGI antibody for use in inhibiting MDGI expression or function in the tumor or metastatic lesion by the aid of said antibody. As another example, disclosed is siRNA or shRNA for inhibiting MDGI expression or function in the tumor or metastatic lesion in a brain, metastatic brain lesions or other brain tumor types. As another example, disclosed is a composition comprising anti-MDGI antibody or siRNA or shRNA for silencing MDGI for use in treating brain tumor or metastatic lesions in the brain or other brain tumor types.

Also disclosed are methods comprising administering a labeled anti-MDGI antibody to a patient, where the labeled anti-MDGI antibody comprises an anti-MDGI antibody conjugated to a detectable label, and detecting the label. The presence and/or location of the label indicates the presence and/or location of brain tumor or metastatic brain lesions or other brain tumor types in the patient. In some forms, the method can further comprise determining the level of MDGI in a sample obtained from a patient by quantitating the detected label, and comparing the level of MDGI in the sample with the level of MDGI in a control sample. A difference in the amount of MDGI in the sample relative to the control sample is indicative of the presence or grade of brain tumor or metastatic brain lesions or other brain tumor type. In some forms, the label can be detected via imaging of the brain.

In some forms, the method can further comprise surgical removal of the brain tumor or metastatic brain lesions or other brain tumor types guided by the location of the label. In some forms, the method can further comprise administering to the patient an effective amount of a pharmaceutical composition comprising anti-MDGI antibody or siRNA or shRNA for MDGI. In some forms, the method can further comprise combining the administration of the pharmaceutical composition with cancer therapies.

In some forms, the method can further comprise monitoring the efficacy of therapy or relapse after the surgical removal of the brain tumor or metastatic brain lesion or other type of tumor tissue in brain. In some forms, the efficacy of therapy or relapse can be monitored by detecting the presence and/or location of brain tumor or metastatic brain lesions or other brain tumor types in the patient by the presence and/or location of a labeled anti-MDGI antibody administered to the patient.

Also disclosed are methods comprising administering to a patient in need of such therapy an effective amount of a pharmaceutical composition comprising anti-MDGI antibody or siRNA or shRNA for MDGI. In some forms, the method can further comprise combining the administration of the pharmaceutical composition with cancer therapies. In some forms, brain tissue of the patient can exhibit detectable MDGI.

Also disclosed are methods comprising determining the level of MDGI in a sample obtained from a patient, comparing the level of MDGI in the sample with the level of MDGI in a control sample, and administering an effective amount of a pharmaceutical composition comprising anti-MDGI antibody or siRNA or shRNA for MDGI in patients in which a difference in the amount of MDGI in the sample relative to the control sample is detected. In some forms, the method can further comprise combining the administration of the pharmaceutical composition with cancer therapies.

Also disclosed are CooP peptides for use in diagnosing or treating brain tumor or metastatic brain lesions or other brain tumor types. Also disclosed are CooP peptides for use in targeting pharmaceutically active agents to brain tumor or metastatic brain lesions or other brain tumor types. Also disclosed are CooP peptides for use in inhibiting MDGI expression or function in a brain tumor or metastatic brain lesions or other brain tumor types by the aid of said antibody.

Also disclosed is use of the MDGI levels obtained in the disclosed method for monitoring the efficacy of therapy or relapse after the surgical removal of the brain tumor or metastatic brain lesion or other type of tumor tissue in brain.

In general terms, in different forms of the disclosed methods and compositions, MDGI presence, location, and/or levels can be detected. The detected MDGI presence, location, and/or levels can be used for a variety of purposes. For example, the presence and/or levels of MDGI can indicate the presence or grade of brain tumors or metastatic brain lesions or other brain tumor types. The location of MDGI can indicate where cancer cells or tumors are present; in particular, locations where more severe or dangerous (e.g., metastatic) cancer cells or tumors are present. The presence, location, and/or levels of MDGI can indicate, for example, whether the patient's cancer is better or worse and/or is or is not responding to therapy. Thus, detection of the presence, location, and/or levels of MDGI can be used to monitor therapy and/or the condition of patient's disease. In this way, the patient's prognosis can be determined, estimated, and/or assessed. Generally, detection of the presence, location, and/or levels of MDGI can be accomplished using compounds or compositions that bind to, target, and/or home to MDGI. For example, anti-MDGI antibodies and/or peptides that bind to MDGI, such as CooP peptide, can be used in conjugates that can bind to, target, and/or home to MDGI. A label in the conjugate can then be used to detect, quantitate, and/or image MDGI present in tissue and/or samples.

Some forms of the disclosed methods and compositions can be used to treat brain tumors, metastatic brain lesions, and/or other brain tumor types. For example, the location of brain tumors, metastatic brain lesions, and/or other brain tumor types determined using the disclosed methods can be used to guide surgical removal of the brain tumors, metastatic brain lesions, and/or other brain tumor types. As another example, administered therapeutics can be targeted to brain tumors, metastatic brain lesions, and/or other brain tumor types using compounds or compositions that bind to, target, and/or home to MDGI. For example, anti-MDGI antibodies and/or peptides that bind to MDGI, such as CooP peptide, can be used in conjugates that can bind to, target, and/or home to MDGI. A therapeutic compound in the conjugate can then have an effect on the brain tumor, metastatic brain lesions, and/or other brain tumor type.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

I. DEFINITIONS

"Activity" as used herein refers to a biological activity.

The term "conjugate" refers to a compound comprising two or more molecules bound together, optionally through a linking group, to form a single structure. The binding can be made by a direct connection (e.g., a chemical bond) between the molecules or by use of a linking group.

"Effective amount" of a compound as used herein is refers to a nontoxic but sufficient amount of the compound to provide the desired result. As will be pointed out elsewhere herein, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

By "an efficient amount" of a pharmaceutical composition is meant an amount efficient to have an effect to the condition of the patient.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

A "grade of brain tumor" as used herein refers to the classification of brain tumors, which is based on the premise that each type of tumor results from the abnormal growth of a specific cell type. To the extent that the behavior of a tumor correlates with basic cell type, tumor classification dictates the choice of therapy and predicts prognosis. For example, WHO grading of astrocytic tumors divide the tumors to 4 grades:

I pilocytic astrocytoma;
II astrocytoma;
III anaplastic (malignant) astrocytoma;
IV glioblastoma.

"Inhibit" as used herein means to reduce or decrease in activity or expression. This can be a complete inhibition of activity or expression, or a partial inhibition. Inhibition can be compared to a control or to a standard level. Inhibition can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent of the control or standard level.

"In need of treatment" as used herein refers to a judgment made by a caregiver (e.g., physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that includes the knowledge that the subject is ill, or will be ill, as the result of a condition that is treatable.

"High," "higher," "increases," "elevates," or "elevation" refer to increases above basal levels, e.g., as compared to a control. The terms "low," "lower," "reduces," or "reduction" refer to decreases below basal levels, e.g., as compared to a control.

"Non-natural amino acid" as used herein refers to an organic compound that has a structure similar to a natural amino acid so that it mimics the structure and reactivity of a natural amino acid. The non-natural amino acid as defined herein generally increases or enhances the properties of a peptide (e.g., selectivity, stability) when the non-natural amino acid is either substituted for a natural amino acid or incorporated into a peptide.

"Modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist."

"Monitoring" as used herein refers to any method in the art by which an activity can be measured.

"Patient" as used herein refers to a subject afflicted with a disease or disorder. The term "patient" includes human and veterinary subjects.

"Peptide" as used herein refers to a class of compounds composed of amino acids chemically bound together. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides.

"Pharmaceutically acceptable" is used herein to refer to a material that is not biologically or otherwise undesirable, i.e., the material can be administered to an individual along with the selected compound without causing any undesirable biological effects or interacting in a deleterious manner with any of the other components of the pharmaceutical composition in which it is contained.

"Pharmacological activity" as used herein refers to the inherent physical properties of a peptide or polypeptide. These properties include but are not limited to half-life, solubility, and stability and other pharmacokinetic properties.

"Providing" as used herein refers to any means or manner of adding a compound or molecule to something else, such as something known in the art. Examples of providing can include the use of pipettes, pipettemen, syringes, needles, tubing, guns, etc. This can be manual or automated. It can include transfection by any means or manner of providing nucleic acids to, for example, dishes, cells, tissue, cell-free systems and can be in vitro or in vivo.

"Preventing" as used herein refers to administering a compound prior to the onset of clinical symptoms of a disease or conditions so as to prevent a physical manifestation of aberrations associated with the disease or condition.

"Sample" are used herein refers to a biological sample from a patient, preferably a blood or fractions of blood sample, typically a plasma or serum or tumor tissue sample obtained from a patient diagnosed, suspected, or postulated to have brain tumor, metastatic brain lesions, or other brain tumor types. By "a control sample" is meant a biological sample from a person not having the disease the patient is diagnosed or postulated to have.

"siRNA" refers to a small interfering RNA, commonly 18 to 30 nucleotides, preferably 20 to 25, more preferably 21 to 23, or approximately 22 nucleotide double-stranded RNA. Preferably at least one strand has a 5'- and/or 3' overhang of 1 to 5, preferably 1 to 3, or 2 nucleotides. siRNA is involved in the RNA interference pathway where the siRNA interferes with the expression of a specific gene.

"shRNA" refers to a short hairpin RNA structure that forms a tight hairpin turn, which can also be used to silence gene expression via RNA interference. The shRNA hairpin structure is cleaved by the cellular machinery into siRNA, which is then bound to the RNA-induced silencing complex (RISC). This complex binds to and cleaves mRNA, which matches the siRNA that is bound to it.

"Silencing" as used herein refers to RNA-mediated inhibition of via RNA interference. Silencing generally is mediated by the RNA-induced silencing complex (RISC).

"Subject" as used herein includes, but is not limited to a human, horse, pig, rabbit, dog, sheep, goat, non-human primate, cow, cat, guinea pig, etc. The term does not denote a particular age or sex. Thus, adult and newborn subjects, as well as fetuses, whether male or female, are intended to be covered.

"Treatment" and "treating" are meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

II. COMPOSITIONS

Diagnostic or imaging compositions containing an anti-MDGI antibody, or a peptide or other molecule recognizing MDGI, and a detectable label are provided. The composition can be used in diagnosing invasive brain tumor or metastatic brain lesions or other brain tumor types.

The compositions described herein are also useful for targeted therapy of invasive brain cancer or metastatic brain lesions, or other tumor types comprising administration of an effective amount of a pharmaceutical composition to a patient. The compositions described herein are also useful for targeted therapy of invasive brain cancer or metastatic brain lesions, or other tumor types comprising administration of an efficient amount of a pharmaceutical composition to a patient. In some embodiments for targeted delivery to the brain, anti-MDGI antibody and nucleic acids disclosed herein are conjugated to CooP. The anti-MDGI antibodies described herein can also be used for targeted delivery of cancer therapeutics to the brain.

The antibodies, peptide or other molecule can be provided as a pharmaceutical composition, in association with a pharmaceutically active agent. A pharmaceutical composition can be prepared by combining a pharmaceutically acceptable excipient, carrier, diluents, buffer, stabilizer or other materials well known to those skilled in the art with the pharmaceutically active agent, e.g., anti-MDGI antibody, other molecule binding to MDGI. The composition is suitable to be administered via a suitable route, preferably a solution for injection intravenously to a patient. Thus, anti-MDGI antibody or other molecules recognizing MDGI or a pharmaceutical composition comprising them may be administered via various routes, typically via intravenous or oral administration or tissue injection. Preferably they are administered via intravenous administration.

(i) Anti-MDGI Antibodies and Other Molecules Binding to MDGI Antibodies and Peptides Antibodies including monoclonal and polyclonal antibodies, fragments and chimeras, may be prepared using methods known to those skilled in the art. The concentration of the anti-MDGI antibody or other molecule in a pharmaceutical composition may vary in wide ranges and depends for example on the tumor type, grade of tumor, nature of the antibody, other molecule or peptide or condition of the patient. Generally the administrated amount is 0.01-100 mg/kg, typically 0.1-50 mg/kg.

A suitable molecule for recognition of MDGI is in addition to anti-MDGI antibody the CooP peptide described in WO 2009/136007. CooP is a nine amino acid long peptide CGLSGLGVA (SEQ ID NO:5).

Antibodies recognizing MDGI are commercially available, for example from Santa Cruz Biotechnology, USA or LifeSpan BioSciences, Inc. In a preferred embodiment, an antibody used in the disclosed methods is MDGI in a biological sample is a monoclonal antibody.

A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, *Nature,* 256:495-497 (1975), the disclosure of which is herein incorporated by reference. An exemplary hybridoma technology is described by Niman et al., *Proc. Natl. Acad. Sci. U.S.A.,* 80:4949-4953 (1983). Other methods of producing monoclonal antibodies, a hybridoma cell, or a hybridoma cell culture are also well known. See, e.g., Antibodies: A Laboratory Manual, Harlow et al., Cold Spring Harbor Laboratory, 1988; or the method of isolating monoclonal antibodies from an immunological repertoire as described by Sasatry, et al., *Proc. Natl. Acad. Sci. USA,* 86:5728-5732 (1989); and Huse et al., *Science,* 246:1275-1281 (1981).

Monoclonal antibodies specific for MDGI can be used in screening assays to detect the presence of this molecule in both liver tumor tissues and serum of hepatocellular carcinoma (HCC) patients. These monoclonal antibodies can also be used as vehicles to deliver cargos, such as nucleic acid, drug or toxin, to liver tumor cells with high expression of CDH17 on cell surface or simply as MDGI antagonists to inhibit MDGI activity in the tumor cell. In addition, hybridoma cell lines provide unlimited source for producing monoclonal antibodies when needed. Culturing the hybridoma cells can produce large quantities of the antibodies economically.

The antibodies or peptides recognizing MDGI may be immobilized on a carrier. Examples of suitable carriers are agarose, cellulose, dextran, Sephadex, Sepharose, liposomes, carboxymethyl cellulose polystyrene, filter paper, ion-exchange resin, plastic film, plastic tube, glass beads, polyamine-methyl vinyl ether-maleic acid copolymer, amino acid copolymer, ethylene-maleic acid copolymer, nylon, silk, etc. The carrier may be in the shape of, for example, a tube, test plate, well, beads, disc, sphere, etc. The immobilized antibody may be prepared by reacting the material with a suitable insoluble carrier using known chemical or physical methods, for example, cyanogen bromide coupling.

Variants of the CooP peptide can also be used. Disclosed are isolated peptides comprising an amino acid segment comprising the amino acid sequence of SEQ ID NO: 5. The isolated peptides can comprise, for example, an amino acid segment comprising, for example, the amino acid sequence of SEQ ID NO: 5 having one or more conservative amino acid substitutions. The amino acid segment can comprise an amino acid sequence at least about 90%, 80%, 70%, or 60% identical to the amino acid sequence of SEQ ID NO: 5 or any percentage in between that represents a change, including addition or deletion, of one or more amino acid. The amino acid segment can comprise the amino acid sequence of SEQ ID NO: 5. The amino acid segment can comprise the amino acid sequence of SEQ ID NO: 5 having one, two, three, four, five, six, seven, eight, or nine conservative amino acid substitutions. The disclosed peptides can consist of the amino acid segment.

The amino acid segment can be, for example, non-circular, linear, circular or cyclic. The amino acid segment can be circularized or cyclized via any suitable linkage, for example, a disulfide bond. The peptide can have any suitable length, such as a length of less than 100 residues. The peptide can have a length of, for example, less than 50 residues. The peptide can have a length of, for example, less than 20 residues.

The disclosed peptides can selectively home to tissue expressing MDGI, such as brain tumors and metastatic brain lesions. The disclosed peptides can selectively interact with such tissue or tumors.

Also disclosed are isolated peptides which have a length of less than 100 residues and which include the amino acid sequence SEQ ID NO: 5 or a peptidomimetic thereof. Such an isolated peptide can have, for example, a length of less than 50 residues or a length of less than 20 residues. In particular embodiments, disclosed can be a peptide that includes the amino acid sequence SEQ ID NO: 5 and has a length of less than 20, 50 or 100 residues.

The disclosed peptides can be in isolated form. As used herein in reference to the disclosed peptides, the term "isolated" means a peptide that is in a form that is relatively free from material such as contaminating polypeptides, lipids, nucleic acids and other cellular material that normally is associated with the peptide in a cell or that is associated with the peptide in a library or in a crude preparation.

The disclosed peptides can have any suitable length. The disclosed peptides can have, for example, a relatively short length of less than ten, 11, 12, 13, 14, 15, 20, 25, 30, 35 or 40 residues. The disclosed peptides also can be useful in the context of a significantly longer sequence. Thus, the peptides can have, for example, a length of up to 50, 100, 150, 200, 250, 300, 400, 500, 1000 or 2000 residues. In particular embodiments, a peptide can have a length of at least 10, 20, 30, 40, 50, 60, 70, 80, 90, 100 or 200 residues. In further embodiments, a peptide can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent than those discussed above. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Also disclosed are chimeric proteins containing a disclosed peptide fused to a heterologous protein. In one embodiment, the heterologous protein can have a therapeutic activity such as cytokine activity, cytotoxic activity or pro-apoptotic activity. In a further embodiment, the heterologous protein can be an antibody or antigen-binding fragment thereof. In other embodiments, the chimeric protein includes a peptide containing the amino acid sequence SEQ ID NO: 5, or a conservative variant or peptidomimetic thereof, fused to a heterologous protein. The term "heterologous," as used herein in reference to a protein fused to the disclosed peptides, means a protein derived from a source other than the gene encoding the peptide or from which the peptidomimetic is derived. The disclosed chimeric proteins can have a variety of lengths including, but not limited to, a length of less than 100 residues, less than 200 residues, less than 300 residues, less than 400 residues, less than 500 residues, less than 800 residues or less than 1000 residues.

As used herein, "chimera" and "chimeric" refer to any combination of sequences derived from two or more sources. This includes, for example, from single moiety of subunit (e.g., nucleotide, amino acid) up to entire source sequences added, inserted and/or substituted into other sequences. Chimeras can be, for example, additive, where one or more portions of one sequence are added to one or more portions of one or more other sequences; substitutional, where one or more portions of one sequence are substituted for one or more portions of one or more other sequences; or a combination. "Conservative substitutional chimeras" can be used to refer to substitutional chimeras where the source sequences for the chimera have some structural and/or functional relationship and where portions of sequences having similar or analogous structure and/or function are substituted for each other. Typical chimeric and humanized antibodies are examples of conservative substitutional chimeras.

Also disclosed are bifunctional peptides which contains a homing peptide fused to a second peptide having a separate function. Such bifunctional peptides have at least two functions conferred by different portions of the full-length molecule and can, for example, display anti-cancer activity or pro-apoptotic activity in addition to selective homing activity.

Also disclosed are isolated multivalent peptides that include at least two subsequences each independently containing a homing molecule (for example, the amino acid sequence SEQ ID NO: 5, or a conservative variant or peptidomimetic thereof). The multivalent peptide can have, for example, at least three, at least five or at least ten of such subsequences each independently containing a homing molecule (for example, the amino acid sequence of SEQ ID NO: 5, or a conservative variant or peptidomimetic thereof). In particular embodiments, the multivalent peptide can have two, three, four, five, six, seven, eight, nine, ten, fifteen or twenty identical or non-identical subsequences. In a further embodiment, the multivalent peptide can contain identical subsequences, which consist of a homing molecule (for example, the amino acid sequence SEQ ID NO: 5, or a conservative variant or peptidomimetic thereof). In a further embodiment, the multivalent peptide contains contiguous identical or non-identical subsequences, which are not separated by any intervening amino acids. In yet further embodiments, the multivalent peptide can be cyclic or otherwise conformationally constrained. In one example, the peptide can be circularized or cyclized via a disulfide bond.

If desired, an isolated peptide, or a homing molecule as discussed further elsewhere herein, can be cyclic or otherwise conformationally constrained. As used herein, a "conformationally constrained" molecule, such as a peptide, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization as discussed further elsewhere herein.

As used herein in reference to a peptide, the term "cyclic" means a structure including an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof.

A peptide also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (orn), α,β-diamino-propionic acid, γ-amino-adipic acid (Adp) and M-(aminomethyl)benzoic acid (Mamb). Cyclization additionally can be effected, for example, through the formation of a lysinonorleucine bond between lysine (Lys) and leucine (Leu) residues or a dityrosine bond between two tyrosine (Tyr) residues. The skilled person understands that these and other bonds can be included in a cyclic peptide.

(ii) MDGI Inhibitory Nucleic Acids

Also disclosed are compositions comprising anti-MDGI antibody or siRNA or shRNA for silencing MDGI for use in treating other tumor types.

MDGI expression can also be inhibited using an antisense nucleic acid. An "antisense" nucleic acid sequence (antisense oligonucleotide) can include a nucleotide sequence that is complementary to a "sense" nucleic acid encoding a protein, e.g., complementary to the coding strand of a double-stranded cDNA molecule or complementary to the CDH17 mRNA. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence within the MDGI mRNA. An antisense oligonucleotide can be, for example, about 7, 10, 15, 20, 25, 30, 35, 40, 45, 50, 55, 60, 65, 70, 75, 80, or more nucleotides in length.

MDGI expression can be inhibited using ribozymes. A ribozyme having specificity for MDGI mRNA can include one or more sequences complementary to a nucleotide sequence within the MDGI mRNA, and a sequence having a known catalytic sequence responsible for mRNA cleavage (see U.S. Pat. No. 5,093,246 or Haselhoff, et al., *Nature* 334:585-591 (1988)). For example, a derivative of a Tetrahymena L-19 IVS RNA can be constructed in which the nucleotide sequence of the active site is complementary to the nucleotide sequence to be cleaved in the mRNA encoded by a uORF of an extended, overlapping 5'-UTR AS mRNA species (see, e.g., U.S. Pat. No. 4,987,071 and No. 5,116, 742). Alternatively, MDGI mRNA can be used to select a catalytic RNA having a specific ribonuclease activity from a pool of RNA molecules (Bartel, et al., Science, 261:1411-1418 (1993)).

(iii) Other Active Agents

The compositions described herein can be combined with conventional cancer therapeutics. Such therapies are, for example, radiation and anti-cancer or anti-angiogenic therapies. In another embodiment the method further comprises that the targeted therapy is combined with surgery. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

An alkylating agent such as melphalan or chlorambucil also can be a cancer chemotherapeutic agent useful in a conjugate. Similarly, a vinca alkaloid such as vindesine, vinblastine or vinorelbine; or an antimetabolite such as 5-fluorouracil, 5-fluorouridine or a derivative thereof can be a cancer chemotherapeutic agent useful in a conjugate.

A platinum agent also can be a cancer chemotherapeutic agent useful in the compositions or conjugates described herein. Such a platinum agent can be, for example, cisplatin or carboplatin as described, for example, in Crown, *Seminars in Oncol.* 28:28-37 (2001). Other cancer chemotherapeutic agents useful in a conjugate include, without limitation, methotrexate, mitomycin-C, adriamycin, ifosfamide and ansamycins. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed conjugates and methods.

(iv) Conjugates

Disclosed are conjugates which include a moiety and a homing molecule, such as CooP. CooP is used to target delivery of the moiety to the brain. As used herein, the term "moiety" is used broadly to mean a physical, chemical, or biological material that generally imparts a biologically useful function to a linked molecule. For example, the disclosed are conjugates can contain a therapeutic agent linked to a homing molecule that selectively homes to brain tumor. Preferably the moiety is a molecule which inhibits the expression or function of MDGI as described herein, that is usefully targeted to the target of the homing molecule (e.g., CooP). Accordingly, the conjugates described herein include anti-MDGI antibodies and/or the inhibitory nucleic acids described herein, which inhibit the expression or function of MDGI.

The term "homing molecule" as used herein, means any molecule that selectively homes in vivo to a target or site of interest in preference to normal tissue. Similarly, the term "homing peptide" means a peptide that selectively homes in vivo to a target or site of interest. It is understood that a homing molecule that selectively homes in vivo to a target or site of interest can exhibit preferential homing to such a target or site.

By "selectively homes" is meant that, in vivo, the homing molecule binds preferentially to the target as compared to non-target. Such a homing molecule can selectively home, for example, to a site where MDGI is preferentially expressed and/or accessibly expressed. Selective homing to, for example, a target or site of interest generally is characterized by at least a two-fold greater localization at targets or sites of interest, as compared to several tissue types of tissue not a target or site of interest. A homing molecule can be characterized by 5-fold, 10-fold, 20-fold or more preferential localization to a target or site of interest as compared to several or many tissue types that are not the target or site of interest, or as compared to-most or all non-target tissue. Thus, it is understood that, in some cases, a homing molecule homes, in part, to one or more normal organs in addition to homing to the targeted molecule, site, or tissue. Selective homing can also be referred to as targeting.

A variety of therapeutic agents can also be included in the conjugates including, without limitation, cancer chemotherapeutic agents, cytotoxic agents, anti-angiogenic agents, polypeptides, nucleic acid molecules and small molecules. A conjugate containing multiple homing molecules can include, for example, two or more, three or more, five or more, ten or more, twenty or more, thirty or more, forty or more, fifty or more, 100 or more, 200 or more, 300 or more, 400 or more, 500 or more, or 1000 or more homing molecules. Moieties useful in a conjugate incorporating multiple homing molecules include, without limitation, phage, retroviruses, adenoviruses, adeno-associated viruses and other viruses, liposomes. Other moieties include polymeric matrices, non-polymeric matrices, particles such as gold particles, microdevices, nanodevices, and nano-scale semiconductor materials.

A conjugate can contain, for example, a liposome or other polymeric matrix linked to at least two homing molecules. If desired, the liposome or other polymeric matrix can be linked to at least ten, at least 100 or at least 1000 homing molecules. Liposomes can be useful in such conjugates; liposomes consist of phospholipids or other lipids, are nontoxic, physiologically acceptable and metabolizable carriers that are relatively simple to make and administer (Gregoriadis, Liposome Technology, Vol. 1 (CRC Press, Boca Raton, Fla. (1984)). The liposome or other polymeric matrix can optionally include another component such as, without limitation, a therapeutic agent, cancer chemotherapeutic agent, cytotoxic agent, anti-angiogenic agent, polypeptide or nucleic acid molecule. These and other moieties known in the art can be components of a conjugate.

Components of the disclosed conjugates can be combined, linked and/or coupled in any suitable manner. For example, moieties and homing molecules can be associated covalently or non-covalently, directly or indirectly, with or without a linker moiety.

(v) Pharmaceutical Compositions

MDGI inhibitors (also referred to herein as "active compounds") can be incorporated into pharmaceutical compositions suitable for administration. Such compositions typically comprise a pharmaceutically effective amount of a MDGI-inhibiting nucleic acid molecule, peptide, or antibody and a pharmaceutically acceptable carrier. The pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

The compounds described herein can be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, anti-inflammatory agents, anesthetics, and the like.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

In some forms, the polynucleotide MDGI inhibitors are prepared with carriers that will protect against rapid elimination from, or degradation in, the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers. These can be prepared according to methods known to those skilled in the art, for example, as described in U.S. Pat. No. 4,522,811. Strategies that inhibit members of the RNAse A family of enzymes or can otherwise protect polynucleotide MDGI inhibitors from these enzymes may be utilized as described for example in U.S. Pat. No. 6,096,720 (Love et al.). A strategy for the compaction of short oligonucleotides into well-defined condensates may also be used to deliver the CDH17 inhibitory polynucleotides disclosed herein (Sarkar T. et al., *Nucleic Acids Research*, 2005, 33(1):143-151), which is incorporated herein by reference in its entirety.

In some forms, the polynucleotide MDGI inhibitors can be inserted into genetic constructs, e.g., viral vectors, retroviral vectors, expression cassettes, or plasmid viral vectors, e.g., using methods known in the art. The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

III. METHODS OF MAKING AND USING

A. Methods of Making (i) Antibodies Recognizing MDGI

MDGI expression or function is inhibited in the tumor or metastatic brain lesion by the aid of an anti-MDGI antibody. The anti-MDGI antibody, peptides or other molecules recognizing MDGI can be labeled with a detectable label. A detectable label is for example a fluorescence label or radiolabel. In a specific embodiment single photon emission computed tomography-computed tomography (SPECT/CT) imaging is used to visualize brain tumors, when the antibody or a peptide or other molecule recognizing MDGI is labeled with $^{111}$Indium.

Methods of making and labeling antibodies are known in the art.

In order to produce monoclonal antibodies for example, a host mammal is inoculated with a MDGI protein or peptide and then boosted. Spleens are collected from inoculated mammals a few days after the final boost. Cell suspensions from the spleens are fused with a tumor cell in accordance with the general method described by Kohler and Milstein (*Nature*, 1975, 256:495-497). In order to be useful, a peptide fragment must contain sufficient amino acid residues to define the epitope of the MDGI molecule being detected. If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule. The peptide fragments may be synthesized by methods known in the art. Some suitable methods are described by Stuart and Young in "Solid Phase Peptide Synthesis," Second Edition, Pierce Chemical Company (1984).

Alternatively, isolated native MDGI or recombinant MDGI may be utilized to prepare antibodies, monoclonal or polyclonal antibodies, and immunologically active fragments (e.g., a Fab or (Fab)$_2$ fragment), an antibody heavy chain, an antibody light chain, humanized antibodies, a genetically engineered single chain F, molecule (Ladne et al., U.S. Pat. No. 4,946,778), or a chimeric antibody, for example, an antibody which contains the binding specificity of a murine antibody, but in which the remaining portions are of human origin. Preferably, antibodies used in the disclosed methods are reactive against MDGI if they bind with a $K_a$ of greater than or equal to $10^7$ M. In a sandwich immunoassay mouse polyclonal antibodies and rabbit polyclonal antibodies are utilized.

Preferred binding epitopes may be identified from a known MDGI gene sequence and its encoded amino acid sequence and used to generate MDGI antibodies with high binding affinity. Also, identification of binding epitopes on MDGI can be used in the design and construction of preferred antibodies. For example, a DNA encoding a preferred epitope on MDGI may be recombinantly expressed and used to select an antibody which binds selectively to that epitope. The selected antibodies then are exposed to the sample under conditions sufficient to allow specific binding of the antibody to the specific binding epitope on MDGI and the amount of complex formed then detected. Specific antibody methodologies are well understood and described in the literature. A more detailed description of their preparation can be found, for example, in Practical Immunology, Butt, W. R., ed., Marcel Dekker, New York, 1984.

Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (Goding in, Monoclonal Antibodies: Principles and Practice, 2d ed., pp. 104-126, Orlando, Fla., Academic Press).

Methods for conjugating or labeling the antibodies discussed above may be readily accomplished by one of ordinary skill in the art. (See, for example, Imman, Methods In Enzymology, Vol. 34, Affinity Techniques, Enzyme Purification: Part B, Jakoby and Wichek (eds.), Academic Press, New York, p. 30, 1974; and Wilchek and Bayer, Anal. Biochem. 171:1-32, (1988)). An antibody specific for MDGI can be labeled with a detectable substance and localized in biological samples based upon the presence of the detectable substance. Examples of detectable substances include, but are not limited to, the following radioisotopes (e.g., $^3$H, $^{14}$C, $^{35}$S, $^{125}$I, $^{131}$I, $^{111}$Indium), fluorescent labels (e.g., FITC rhodamine, lanthanide phosphors), luminescent labels such as luminol; enzymatic labels (e.g., horseradish peroxidase, beta-galactosidase, luciferase, alkaline phosphatase, acetylcholinestease), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). Indirect methods may also be employed in which the primary antigen-antibody reaction is amplified by the introduction of a second antibody, having specificity for the antibody reactive against MDGI.

(iii) Nuclei Acid Molecules Inhibiting MDGI Expression or Function

The molecule inhibiting MDGI expression or function can be a nucleic acid molecule. MDGI expression or function can be inhibited in the tumor or metastatic brain lesion e.g. by the aid of RNAi technology.

RNA interference (RNAi) is a powerful approach for reducing expression of endogenously expressed proteins. It is widely used for biological applications and is being harnessed to silence mRNAs encoding pathogenic proteins for therapy. Various methods—including delivering RNA oligonucleotides and expressing RNAi triggers from viral vectors—have been developed for successful RNAi in cell culture and in vivo. RNAi is a conserved mechanism of post-transcriptional gene silencing in which small, double-stranded RNAs (siRNA or shRNA) suppress expression of genes bearing a partially complementary sequence. siRNAs can be designed to knock down any known gene. Recently, RNAi-based gene silencing approaches have been demonstrated in humans, and ongoing clinical trials hold promise for treating fatal disorders or providing alternatives to traditional small molecule therapies (Davidson and McCray, *Nature Reviews Genetics*, 12:329-340 (2011). siRNA and shRNA are preferably chemically synthesized. shRNA or siRNA products are commercially available from several suppliers, for example from Santa Cruz Biotechnology, Inc.

MDGI expression can also be inhibited using an antisense nucleic acid. Antisense nucleic acid sequences and delivery methods are well known in the art (Goodchild, *Curr. Opin. Mol. Ther.*, 6(2):120-128 (2004); Clawson, et al., Gene Ther., 11(17):1331-1341 (2004)), which are incorporated herein by reference in their entirety. An antisense nucleic acid sequence can be designed such that it is complementary to the entire MDGI mRNA sequence, but can also be an oligonucleotide that is antisense to only a portion of the CDH17 mRNA. For example, the antisense oligonucleotide can be complementary to a portion of the MDGI enzymatic domain (inositol 5'-phosphatase domain) or a portion of the amino-terminal src-homology domain (SH2). An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection). Other examples of useful antisense oligonucleotides include an alpha-anomeric nucleic acid. An alpha-anomeric nucleic acid molecule forms specific double-stranded hybrids with complementary RNA in which, contrary to the usual beta-units, the strands run parallel to each other (Gaultier et al., *Nucleic Acids. Res.*, 15:6625-6641 (1987)). The antisense nucleic acid molecule can also comprise a 2'-o-methylribonucleotide (Inoue et al. *Nucleic Acids Res.*, 15:6131-6148 (1987)) or a chimeric RNA-DNA analogue (Inoue et al. *FEBS Lett.*, 215:327-330 (1987)).

Ribozymes can also be employed to inhibit MDGI expression. Ribozymes are a type of RNA that can be engineered to enzymatically cleave and inactivate other RNA targets in a specific, sequence-dependent fashion. Ribozymes and methods for their delivery are well known in the art (Hendry, et al., *BMC Chem. Biol.*, 4(1):1 (2004); Grassi, et al., *Curr. Pharm. Biotechnol.*, 5(4):369-386 (2004); Bagheri, et al., *Curr. Mol. Med.*, 4(5):489-506 (2004); Kashani-Sabet M., *Expert Opin. Biol. Ther.*, 4(11):1749-1755 (2004), each of which are incorporated herein by reference in its entirety. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art.

B. Methods of Using

The compositions described herein can be administered using several routes of administration. The compounds and pharmaceutical compositions described herein can be administered to the subject in a number of ways depending on whether local or systemic treatment is desired, and on the area to be treated. Examples of routes of administration include parenteral, e.g., intravenous, intradermal, subcutaneous, oral (e.g., inhalation) and transmucosal. Parenteral administration, if used, is generally characterized by injection. Injectables can be prepared in conventional forms, either as liquid solutions or suspensions, solid forms suitable for solution or suspension in liquid prior to injection, or as emulsions. Another approach for parenteral administration involves use of a slow release or sustained release system such that a constant dosage is maintained. See, e.g., U.S. Pat. No. 3,610,795, which is incorporated by reference herein.

Vectors for targeting molecules across the blood brain barrier are known in the art. For example, lentiviral vectors (including a gene of interest) that can cross the blood brain barrier and method of making them are disclosed for example in U.S. Pat. No. 7,090,837. The MDGI inhibitory molecules described herein are preferably targeted to brain tumors by conjugation to CooP.

Nanoparticles, liposomes and other cationic lipid molecules can also be used to deliver siRNA into animals. It has been shown that siRNAs delivered systemically in a liposomal formulation can silence the disease target apolipoprotein B (ApoB) in non-human primates (Zimmermann, et al., *Nature*, 2006, 441:111-114). A gel-based agarose/liposome/siRNA formulation is also available (Jiamg, et al., *Oligonucleotides*, 14(4):239-48 (2004)). In particular, suitable techniques for cellular administration of the polynucleotide CDH17 inhibitors, in vitro or in vivo are reviewed for example in Borkhardt, *Cancer Cell*, 2:167-8; Hannon, *Nature*, 418:244-51 (2002); McManus, et al., *Nat Rev Genet.*, 3:737-47 (2002); Scherr, et al., *Curr Med. Chem.*, 10:245-56 (2003); Shuey, et al. *Drug Discov Today*, 7:1040-6 (2002); Gilmore, et al., *J. Drug Target.*, 12(6):315-340 (2004); Dykxhoorn, et al., *Annu. Rev. Med.*, 56:401-423 (2005). Systemic delivery using liposomes is disclosed for example in Lewis, et al. *Nat Genet.*, 32:107-8 (2002); Paul, et al. *Nat Biotechnol.*, 20:505-8 (2002); Song, et al., *Nat Med.*, 9:347-51 (2003); Sorensen, et al., *J Mol Biol.*, 327: 761-6 (2003).

The nanoparticles, liposomes, other cationic lipid molecules or other molecule inhibiting MDGI expression or activity can in some embodiments serve as the "moiety" in the CooP conjugates described herein.

By using the products and methods as disclosed herein a difference in the amount of MDGI in the sample of the patient relative to the control sample is indicative of the presence or grade of the brain tumor, metastatic brain lesions or other tumor types. The MDGI levels in blood or fractions of blood, typically serum or plasma can be used in brain tumor diagnostics and make possible to follow up the treatment efficiency and/or tumor progression.

Antibodies or other molecules recognizing MDGI are useful in determining the grade of brain tumor, metastatic brain lesions or other brain tumor types. They can be used as such, or in combination with conventional determination methods, such as methods based on histology, type of vasculars, p53 status, amount of proliferating cells or epidermal growth factor receptor EGFR.

The antibodies or other molecules that recognize MDGI are also useful in a method for determining the presence or grade of brain tumor or metastatic brain lesions or other tumor types in a patient. The level of MDGI is determined in a biological sample obtained from the patient, and compared with the level of MDGI in a control sample. A difference in the amount of MDGI in the sample relative to the control sample is indicative of the presence or grade of brain tumor or other tumor types. In other embodiments, MDGI can be used in a method for determining the presence or grade of other tumor types than brain tumor. Such "other tumor types" are preferably kidney carcinomas, sarcomas, ovarian carcinomas, pancreatic carcinomas, testicular cancers, melanomas and prostate carcinomas. The anti-MDGI antibodies, peptides or other molecule binding MDGI can also be used in a method for diagnosing invasive brain tumor or metastatic brain lesion in a patient, or other tumor types. The method includes conjugating an anti-MDGI antibody or peptide or other molecule recognizing MDGI, to a detectable label, such as an imaging agent. The labeled anti-MDGI antibody or the peptide binding to MDGI is administered to the patient, and the label is detected.

Also within the scope of the methods described herein is the use of anti-MDGI antibodies for diagnosing or treating other tumor types, for use in targeting pharmaceutically active agents to other tumor types for use in inhibiting MDGI expression or function in other tumor types. The anti-MDGI antibody or other molecule recognizing MDGI can be used to target pharmaceutically active agents to brain tumor or metastatic brain lesions or other tumor types. Also within the scope of the methods of treatment described herein is the use of inhibitory nucleic acid molecules such as siRNA or shRNA to inhibit MDGI expression or function in other tumor types. An antibody or other molecule that recognizes MDGI can be used to target imaging agents or anti-cancer therapies to tumor tissue. More specifically, for example the CooP peptide or an antibody or other molecule or peptide that recognizes MDGI can be used to target imaging agents or anti-cancer therapies to tumor tissue.

The methods described herein encompass the use of the MDGI levels for monitoring the efficacy of therapy or relapse after the surgical removal of other tumor types than brain tumor. "Determining the level of MDGI" reflects the effectiveness by which MDGI is expressed, which indicates the invasiveness or aggressiveness of the tumor. Determination of the level of MDGI can be carried out by using anti-MDGI or other molecules recognizing MDGI, for example peptides binding to MDGI.

In one embodiment of the methods described herein, anti-MDGI antibody is conjugated to a detectable label. The labeled anti-MDGI antibody is administered to the patient, and the label is detected.

The methods for targeted therapy can in some embodiments be combined with conventional cancer therapies. Such therapies are for example radiation and anti-cancer or anti-angiogenic therapies. In another embodiment the method further comprises that the targeted therapy is combined with surgery. For example, the method the present with boron neutron capture therapy (BNCT) where tumor cells are irradiated while surrounding healthy tissues are preserved. Boron-10 atoms are capable of capturing low-energy neutrons which leads to a nuclear reaction emitting alpha- and lithium recoil particles. A high intracellular boron-10 concentration is needed at the time of neutron irradiation to maximize a high radiation dose to the tumor. The molecules of the present invention can be used as delivery molecules for boron. After infusion of the anti-MDGI antibody, other molecule or peptide, typically 1 hour after infusion, the tumor is irradiated with neutrons using optimally angled beams.

The disclosed methods include the determination, identification, indication, correlation, diagnosis, prognosis, etc. (which can be referred to collectively as "identifications") of subjects, diseases, conditions, states, etc. based on measurements, detections, comparisons, analyses, assays, screenings, etc. For example, detection of MDGI in brain tissue and/or measurement of a higher level of MDGI in brain tissue can identify a subject having MDGI-related cancer or a subject that can be treated with an anti-MDGI based treatment or MDGI-targeted treatment. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different measurements, detections, comparisons, analyses, assays, screenings, etc., and the like.

For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

EXAMPLES

Identification of MDGI as the Binding Partner for CooP

MDGI was found to be the receptor/binding partner for the CooP peptide.

Low grade astrocytomas, a class of malignant brain tumors, acquire their blood supply by co-opting existing normal blood vessels and propagating along them without initiating angiogenesis. This leads to diffuse invasion of tumor cells over long distances in the brain without formation of real tumor masses. The most malignant form of astrocytomas, also called glioblastoma multiforme (GBM), become highly vascularized and tumors appear more local than the low-grade astrocytomas. To date very little is known about the molecular patterning typical for the low-grade glial tumors. In vivo phage display is a powerful method to isolate homing peptides and map the vascular diversity of tumors as well as other organs. Efficient tissue diffusion and good target accessibility make homing peptides excellent probes for biodistribution studies and non-invasive tumor imaging. Phage displayed peptide libraries were used to identify a peptide that very specifically homes to malignant brain tumors.

Both in vitro and in vivo data provided herein show that the mammary-derived growth inhibitor (MDGI) is the receptor molecule that the CooP peptide recognizes within the tumors and tumor-associated vasculature. Furthermore, the data provided herein show that MDGI is expressed in clinical brain tumor specimens in a grade-dependent fashion, which led to the discovery of MDGI as a novel marker for malignant brain tumors. A brain tumor homing peptide was labeled with $^{111}$Indium and used it in single photon emission computed tomography-computed tomography (SPECT/CT) imaging to visualize brain tumors in vivo. The high specificity and targeting potential of the peptide shows that the peptide is useful for detection and eradication of tumor satellites left behind after the surgical resection of the primary tumor.

To identify protein candidates typical for infiltrative astrocytomas an in vivo phage display screen was performed using a tumor model mimicking the low-grade astrocytoma phenotype (Blouw et al., *Cancer Cell*, 4:133-146 (2003)). The isolation of a peptide named "CooP" (homing specifically to the low-grade astrocytoma islets harboring co-opted blood vessels) is described below. The specificity of homing was confirmed using fluorescein-labeled peptides and whole-body scintigraphic imaging (SPECT/CT) with the radiolabeled CooP peptide. Also described herein is the identification of mammary-derived growth inhibitor, MDGI/H-Fabp/Fabp3, as the receptor for the CooP peptide in the brain tumor tissue. In addition, the presence of MDGI in the tumor vasculature, being readily accessible for intravenously injected agents, was investigated. Furthermore, the data shows that MDGI is expressed in the human brain tumor specimens in a grade-dependent manner.

To identify the receptor for the peptide a yeast-two-hybrid screen was performed. The peptide sequence was introduced into a bait plasmid and co-transformed to bacteria with the target plasmids encoding a murine embryonic (E12.5) cDNA library. Three of the hits represented two different cDNAs for the mammary-derived growth inhibitor (MDGI; NM_004102) also known as heart type fatty acid binding protein (H-FABP or FAPB-3). MDGI expression in the transiently transfected U2OS cells increased the CooP displaying phage binding 10-fold compared to the original library.

In the next set of examples, MDGI expression was studied in the human glioblastoma xenograft tumors (U87MG), and in muscle, heart, and brain tissues using anti-MDGI antibodies. To visualize the blood vasculature, mice carrying intracranial xenografts (U87MG) were perfused with FITC-lectin (from *Lycopercicon esculanta*). The results showed that MDGI was expressed in the tumor, muscle, and heart, but MDGI expression could not be detected in the brain. Interestingly, MDGI showed vasculature-associated expression only in the tumors.

Other experiments determined whether MDGI is accessible via the circulation to act as a receptor/binding partner for systemically administered molecules, such as anti-MDGI antibody. The anti-MDGI antibody was administered intravenously to intracranial tumor bearing mice (U87MG) followed by histological analysis of tissues. The anti-MDGI antibody accumulated in the tumor tissue but could not be detected in any other tissue studied, while the control antibody (Goat IgG) did not accumulate in tumor vasculature or in any other tissue examined.

The methods and compositions described herein were exemplified by using commercially available anti-MDGI-antibodies, but the antibodies could be produced, for example, by using the MDGI sequences or parts thereof. Antibodies recognizing MDGI are commercially available, for example from Santa Cruz Biotechnology, USA or LifeSpan BioSciences, Inc.

Materials and Methods

Cell Lines

Hif-1α-deficient (HIFko) mouse astrocytes were propagated as previously described (Blouw et al., Cancer Cell, 4:133-146 (2003)). MDA-MB-231 breast carcinoma cells were cultured in the RPMI 1640 supplemented with 10% FCS, 2 mM L-glutamine, 100 U/ml penicillin and 100 μg/ml streptomycin. U87MG human glioma cells and $BT_4C$ rat glioma cells were maintained in DMEM supplemented with 10% FCS, 2 mM L-glutamine, 100 U/ml penicillin and 100 μg/ml streptomycin. U2-OS osteosarcoma cells (a kind gift from Dr. Marikki Laiho, University of Helsinki, Finland) were cultured in DMEM and 15% FCS. All cells were cultured in a humidified 5% $CO_2$ atmosphere at 37° C.

Tumor Xenografts

Athymic female Balb/c nu-nu mice (4-6 wks) from Taconic Europe were used in all tumor experiments. Establishment of the intracranial tumors has been described (Blouw et al., 2003). In brief, 50 000 HIFko, VEGF+, U87MG, U87-GFP, U87-MDGI-GFP or $BT_4C$ tumor cells in phosphate buffered saline (PBS) or DMEM were injected through the skull using a Hamilton syringe (no 84855), 2 mm right from the bregma at the depth of 3 mm in the brain parenchyma. Mice were used for some experiments 10-15 days after tumor cell inoculation. In experiments studying the role of MDGI in tumor progression and invasiveness, mice were used 10-21 days after tumor cell inoculation. To establish subcutaneous tumors, $2-5\times10^6$ cells were grafted subcutaneously on the abdominal side of the mice (in some experiments) or into the mammary fat pad, in other experiments. All animal studies were conducted according to the guidelines of the Provincial Government of Southern Finland and the protocol was approved by the Experimental Animal Committee.

Phage Display and In Vivo Biopanning

An NNK-encoded $CX_7C$ peptide library (a kind gift from Dr. Erkki Ruoslahti, Burnham Institute, Santa Barbara, USA) was used on the T7Select415-1-phage (Novagen, USA). Phage selections were performed as previously described (Hoffman et al., 2004, n Phage Display, T. Clackson, and H. B. Lowman, eds. (Oxford, U.K: Oxford University Press), pp. 171-192; Rivinoja and Laakkonen, Methods Mol Biol 683, 401-415 (2011)). For each round of selection, brain tumor-derived cell suspension was prepared using Collagenases II and IV (Worthington, Lakewood, USA). For the first ex vivo round of panning tumor-derived cell suspension was incubated overnight at 4° C. with $5\times10^9$ plaque-forming units (PFU) of the $CX_7C$ library. Cells were washed extensively with PBS/1% BSA. The bound phage was rescued and amplified in E. coli (BLT5615, Novagen, USA), and used for a second round of ex vivo selection. The ex vivo enriched phage pool was injected into the tail vein of intracranial HIFko tumor-bearing mice, and allowed to circulate for 15 min. To remove unbound phage, animals were perfused through the left ventricle of the heart with PBS. Brain, including the tumor, was excised, and the recovered and amplified phage was used for the next found of in vivo panning. The in vivo selection procedure was repeated three times. In each round, non-recombinant control phage was injected to a separate mouse to assess the background. The relative phage titers were determined as the ratio of specific phage and non-recombinant control phage recovered from the tumor tissue.

Peptide Synthesis

Tumor specific peptide CooP ($NH_2$-ACGLSGLGVA-$CONH_2$; SEQ ID NO:8) and its control ($NH_2$-ACVAAL-NADG-$CONH_2$; SEQ ID NO:7) were synthesized using an Apex 396 DC multiple peptide synthesizer (Advanced ChemTech, Louisville, Ky.) with Fmoc strategy and O-Benzotriazole-N,N,N',N'-tetramethyl-uronium-hexafluorophosphate (HBTU, GLS Biochem, Shanghai, China) and N,N-diisopropylethylamine (DIPEA, Fluka, Steinheim, Germany) as coupling reagents. Rink resin was used as the solid phase (Novabiochem, Laufelfingen, Switzerland) to produce carboxyl terminal amide. Synthesized peptides were left on resin for further conjugations. DTPA was conjugated directly to the alpha-amino group of the peptide using tertbutyl protected DTPA (diethylenetriamine-N,N,N'',N'''-tetra-tert-butyl acetate-N'-acetic acid, Macrocyclics, Dallas, Tx) where 4/5 carboxylic acids were protected. DTPA was conjugated via one free carboxylic acid using HBTU/DIPEA as coupling reagents. After cleavage four carboxylic acids remained free for chelation.

Isothiocyanate activated fluorescein (FITC; Sigma, St. Louis, Mo.) was conjugated to the peptides on resin via the side chain of the additional amino terminal lysine to avoid the spontaneous cleavage during the strong acid treatment. After removal of Fmoc group using 20% piperidine in dimethyl formamide (DMF) the free N-terminus was acetylated with 20% acetic anhydride in DMF. The acid labile methyltrityl (Mtt) protection group of the additional lysine was removed with 2% trifluoroacetic acid (TFA) in DCM. FITC (2 mg from the stock solution of 10 mg/ml in DMF) was added into reaction mixture following addition of 15 μl triethanolamine (TEA). Resin was mixed for 1 h. FITC conjugation step was repeated to gain maximal yield of FITC conjugated peptides. Conjugated peptides were cleaved from the resin using a mixture of 95% TFA, 3% ethanedithiol (EDT), 1% triisopropylsilane (TIS) and 1% $H_2O$ where EDT and TIS were used as scavengers.

Peptides were purified with RP-HPLC (Shimadzu, Kioto, Japan) using $C_{18}$ reverse phase column (xTERRA, $250\times10$ mm, Waters, Milford, Mass.), and acetonitrile gradient (ACN, 0-95%, 45 min). The peptides were verified by mass spectrometry on an ABI QSTAR XL hybrid mass spectrometer using MALDI interface (Applied Biosystems, Foster City, Calif.) and the purity was determined by an analytical HPLC (Shimadzu. Kioto, Japan) on a $240\times1.4$ mm $C_{18}$ column (xTERRA) eluted with 0-60% ACN for 30 minutes.

Radiolabeling

The DTPA conjugated peptides (20 μg per animal) were mixed with 0.2 M NaAc (pH 5) and 5 MBq of $^{111}$Indium-chloride ($^{111}InCl_3$, Mallinckrodt, Le Petten, Netherlands)

per animal was added to the mixture. The total volume of the solution was calculated to be 100 µl/animal. The reaction mixture was incubated for an hour at RT and the radiochemical purity was measured by using an instant thin-layer chromatography (ITLC-SG, Pall Corporation, USA) on a 13×1.5 cm strip using 0.3 M NaCit (pH 5) as a mobile phase. The radiochemical purity of the peptides was 99-100%.

SPECT/CT Imaging

The imaging studies were performed two weeks post U87MG tumor implantation. For SPECT/CT (single photon emission computed tomography-computed tomography) imaging animals were anesthetized with 1-3% isoflurane in $N_2/O_2$ at a 70:30 ratio. The radiolabeled peptide (100 µl) was injected into the tail vein followed by SPECT imaging using a combined small animal SPECT/CT (Gamma Medica Inc., Northridge, Calif.) with dual gamma camera modality. Medium energy parallel hole collimators were used in all gamma imaging with a 171/245/416 keV energy window for $^{111}$In. Planar two-dimensional imaging for all animals was performed at earliest possible time point after injection with 60 s acquisition time/image up to 30 minutes. For 3D imaging total of 64 projections, (120 s/projection) were used. The matrix size was 80×80 in 125×125 mm² field of view (FOV). CT imaging was performed using the same coordinates as SPECT with 512 projections, 1024×1024 projection matrix size and a voltage of 60 kV.

The planar SPECT images were combined to X-ray image with an in-house Matlab software (The MathWorks Inc. Natick, Mass.). Three-dimensional SPECT reconstruction was carried out using the LumGem software (Gamma Medica, Northridge, Calif., USA) with Butterworth six-order low-pass post-filtering with cutoff frequency of 0.3. The abdomen of the animal was masked to reduce noise from kidneys and bladder. 3D images with dimensions of 512×512×512 matrix size in 87×87×87 mm³ FOV were obtained. Both CT and SPECT images were interpolated into final 256×256×256 size by using commercial software (Gamma Medica, Northridge, Calif., USA). The images were combined using IDL software (ITT Visual Information Solutions, Washington, Va.), and monitored with the Amira software (Mercury, Carlsbad, Calif.).

Analysis of the Radioactivity in Different Organs

After the last imaging session animals were sacrificed with $CO_2$ and tissue samples were collected. Major organs and tissues (blood, heart, lungs, liver, spleen, left kidney, duodenum, ovaries, fat, muscle, skin, brain and brain tumor) were weighed, and the radioactivity in each organ or tissue sample was measured in an automated gamma counter (Clinigamma, Turku, Finland). The counts obtained were corrected for the background radiation and physical decay, and tissue radioactivity was expressed as percentage of the injected dose per gram of tissue (% ID/g)±SD.

Detection of Peptides and Antibodies in the Tissues

Intravenously injected fluorescein-labeled peptides (100 µl of 1 mM solution) and antibodies (20 µg/animal) were allowed to circulate for one hour followed by perfusion through the heart with 10 ml of phosphate buffered saline (PBS) and 10 ml of 4% paraformaldehyde (PFA) in PBS. Tumors and organs were excised, PFA-fixed and soaked in 30% sucrose (w/v) overnight. Tissues were frozen in the OCT embedding medium (Tissue-Tek). Sections (5-10 µm) were cut for histological analyses. To detect the in vivo distribution of the fluorescein-labeled peptides, sections were stained with a rabbit anti-FITC antibody (Zymed Laboratories, San Francisco, USA). To visualize blood vessels, MDGI and tumor cells, sections were stained with the rat anti-mouse CD31 (BD Pharmingen), goat or rabbit anti-MDGI (Santa Cruz Biotechnology, USA), or a rabbit anti-SV40 large T antigen (a kind gift from Dr. Hanahan, ISREC, Switzerland) antibodies followed by the Alexa-594 and Alexa-488 conjugated secondary antibodies (Molecular Probes, Eugene, Oreg., USA). Nuclei were visualized with DAPI (Vector Laboratories, Burlingame). Sections were examined under an inverted fluorescence microscope (Axioplan).

Yeast-2-Hybrid Screen

The sense- and antisense oligonucleotides (AATTCT-GCGGACTGAGCGGGTTAGGC GTTGCTG (SEQ ID NO:1), GATCCAGCAACGCCTAACCCGCTCAGTC-CGCAG (SEQ ID NO:2)) purchased from Sigma encoding the CooP sequence were cloned into the pGBKT7 bait vector (Clontech). A mouse embryonic (E12.5) library in the Pad-GAL4-2.1 prey vector was transformed into yeast cells expressing the baits. Clones producing β-galactosidase were isolated, and the prey cDNAs were purified and sequenced. The screen was performed according to the Fields' method (Fields and Song, Nature, 340:245-246 (1989)) at the Yeast Two-Hybrid Core Facility, Biomedicum Helsinki (University of Helsinki, Finland).

Cloning of the MDGI from the Brain Tumor cDNA

Tumor tissue was excised from the brain of intracranial HIFko astrocytoma bearing mice. To disrupt the tumor tissue, the tissue was shaken in a test tube for 5 s in the FastPrep FP 120 (Qbiogene, Carlsbad, USA), a high-speed bench-top reciprocating device designated for disruption of cell membranes. RNA was isolated from the supernatant with the Rneasy kit (Qiagen). A total of 1 µg of RNA, isolated from two tumors, was used for the cDNA synthesis by the QuantiTech RT Kit (Qiagen). Full-length MGDI was cloned using the tumor-derived cDNA as a template with the following primers: fw: GGAATTCGCGGACGCCTTT-GTCGGTACCTGGAAG (SEQ ID NO:3); rev: CCTC-GAGTCACGCCTCCTTCTCATAAGTCCGAGTGCTC (SEQ ID NO:4), and ligated to the pcDNA3-9E10 plasmid (a kind gift from Dr. Päivi M. Ojala, University of Helsinki, Finland).

Transfections and Phage-Binding Assays

For the binding assays U2-OS osteosarcoma cells were transfected with the pcDNA3-9E10 plasmid encoding the full-length MDGI with the FuGENE transfection reagent (Roche) according to the manufacturer's instructions. Cells were plated on 10 cm Ø cell culture dishes 24 hours prior to transfection. Phage displaying either the CooP peptide sequence CGLSGLGVA (SEQ ID NO: 5) or random $CX_7C$ library sequences were incubated with the transfected cells for two hours at 4° C. The unbound phage was removed with extensive washes in PBS/1% BSA. Cells were detached using a plastic scraper and the bound phage was rescued by infecting with bacteria. The binding affinities were determined by phage titration as the ratio of CooP or library phage and non-recombinant control phage recovered from the cells.

To obtain an MDA-MB-231 breast tumor cell line stably expressing the MDGI as a c-Myc fusion protein, cells were transfected with the pcDNA3-9E10-MDGI plasmid as described herein. 24-48 h post-transfection cells were exposed to the G418 (0.7 mg/ml, Sigma) selection. Geneticin-resistant clones were picked by the ring-cloning method, expanded, and subsequently tested for the presence of the transgene expression by immunofluorescence and by Western-blot analyses.

MDGI gene was cloned into a lentiviral pBOB\cag\GFP expression vector (kind gift from Dr. Ylä-Herttuala, University of Eastern Finland, Kuopio, Finland) and transfected into human embryonic kidney cells (293FT, 4×10⁶) using the Lipofectamine™ 2000 (Invitrogen, Carlsbad, Calif., USA). Virus containing supernatants were collected 72 hours post-transfection. To remove cell debris the medium was centrifuged briefly (2 min, 160 g) and filtered through a 0.45 µm filter. The supernatant was concentrated with the Optima L-80 XP ultracentrifuge (Beckmann) supplied with a swinging bucket rotor (SW28, Beckmann coulter). MDA-M-231 and U87MG cells (50% confluent) were transduced with concentrated MDGI-GFP and GFP encoding viruses. Moderately and highly transgene positive cells were sorted by using a BD FACSAria cell sorter (purity mode, BD Biosciences, USA). Expression of the transgenes was verified using Western blot-analyses. The efficiency of transduction was determined using immunofluorescence microscopy by counting the percentage of the transgene expressing cells.

Immunoblot Analysis

The following primary antibodies were used: goat or rabbit polyclonal anti-MDGI antibody (1:200, Santa Cruz Biotechnology, USA), mouse monoclonal anti-c-Myc (9E10) antibody (1:1000, Biocompare), rabbit polyclonal anti-GAPDH antibody (1:1000, Cell Signaling, USA). After extensive washes the membranes were incubated with the horseradish peroxidase-coupled anti-goat, anti-mouse or anti-rabbit antibodies (Dako, Denmark). The bound antibody was detected with the ECL (Pierce).

Immunohistochemistry of Paraffin-Embedded Tissues

Five-micrometer thick, paraffin-embedded tissue sections were prepared for histological analysis. Antigen retrieval was performed by heating the samples in a 10 mM sodium citrate buffer (pH 6.0) using the microwave oven (780 W 5 min, 380 W 10 min) MDGI was detected from the sections using the TSA Indirect Kit (PerkinElmer, Boston, Mass., USA). Nuclei were stained with Hematoxylin.

Human Tumor Material

Formalin-fixed paraffin-embedded tumor tissue samples obtained from patients diagnosed with a brain tumor following craniotomy were retrieved from the archives of the Department of Pathology, Helsinki University Central Hospital, Finland. The brain tumors were originally diagnosed as either pilocytic astrocytoma (grade 1), diffuse astrocytoma (grade 2), anaplastic astrocytoma (grade 3), primary or secondary glioblastoma multiforme GBM (grade 4), medulloblastoma or ependymoma. The histopathological diagnoses were reviewed by professional pathologists (AP and OT) based on the World Health Organization (WHO) criteria. The study was approved by an Ethics Committee of the Helsinki University Central Hospital, Helsinki Uusimaa, Finland. A permission to use tumor tissue for the study was obtained from the Ministry of Social Affairs and Health, Finland.

Targeted Treatment of Tumor Bearing Mice

Immunocompromised (Balb/c nu/nu) mice were implanted with HifKO murine astrocytoma cells (Blouw et al. 2003). Treatment with saline (PBS), free chlorambusil (Cbl) and targeted drug (chlorambusil conjugated to CooP peptide; CooP—CPP-Cbl, 5 mg/kg) was started at day 5 post-implantation and continued every second day until day 14. At day 14 the experiment was ended due to the poor condition of the animals in the PBS and free chlorambusil groups.

Collagen Invasion

Type I collagen from rat tail (C7661, Sigma) was dissolved in 0.2% acetic acid. The collagen was diluted to a final concentration of 2.2 mg/ml in MEM and neutralized with NaOH. Collagen gels were then casted into the upper chamber of cell culture inserts (Falcon) and allowed to polymerize at +37° C. for 1 hour. MDA-MB-231 breast carcinoma cells (1.2×10⁵) in complete RPMI 1640 medium supplemented with 10% FBS were laid on top of the gels. Complete RPMI 1640 medium was added to the lower chamber and the cells were cultured at 37° C. for 14 days, replenishing the medium every second/third day. The gels were then fixed with 3% PFA and embedded into TissueTek.

Results

Identification of Peptides Homing to Malignant Brain Tumors

Figure 1B:
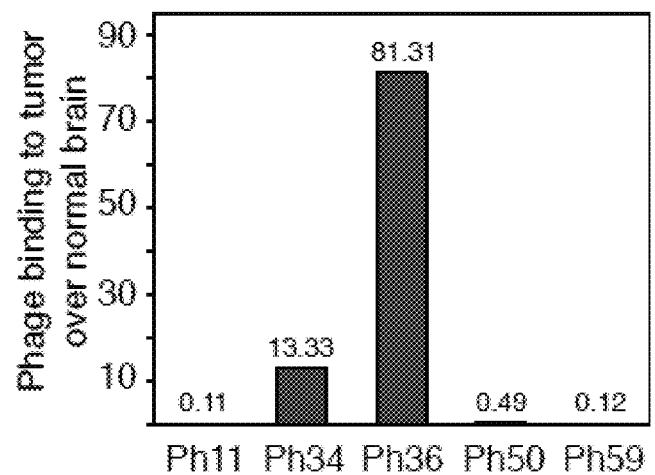
Figure 1C:
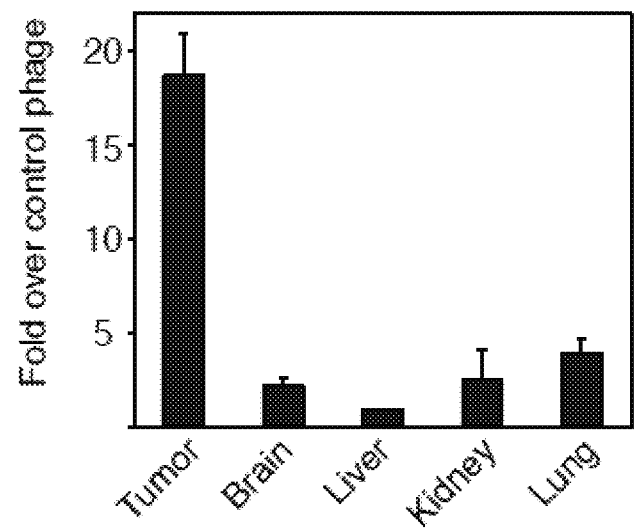

A combined ex vivo/in vivo phage display screen (Hoffman et al., 2004, Rivinoja and Laakkonen) was performed in order to isolate peptides that home specifically to the invasive astrocytoma islets harboring co-opted blood vessels. As a model the hypoxia inducible factor deficient (HIFko) transformed astrocytes, which grow as islets with co-opted blood vessels (Blouw et al. 2003), were used. Two rounds of ex vivo panning with the $CX_7C$ phage displayed peptide library on cell suspensions prepared from the intracranial HIFko tumors yielded a 5-fold enrichment of phage binding to all tumor-derived cells compared to the control phage. This pre-selected phage pool was subjected to in vivo selection to screen for peptides capable of homing to tumor after an intravenous injection. An increase in tumor homing over the control phage from the 95-fold was observed in the first in vivo round to approximately 200-fold in the third round (FIG. 1A). After the third round of biopanning the peptide sequence of approximately 50 randomly selected individual phage clones were analyzed and searched for enriched sequences. Based on the sequence data five clones were selected to further validate their ability to bind and home to the HIFko astrocytomas. Phage 11, 34, 36, 50 and 59 all showed high, up to 1700-fold, ex vivo binding to tumor over the control phage. However, phage 11, 50 and 59 showed even higher affinity for the normal brain tissue (FIG. 1B) suggesting that these phage/peptides were rather brain than brain tumor specific. The brain tumor to normal brain ratio was 13.3 for the phage 34 and over 80 for the phage 36 demonstrating specificity for brain tumor tissue (FIG. 1B). Peptides encoded by phage 34 (CSESGLGVA; SEQ ID NO:6) and 36 (CGLSGLGVA; SEQ ID NO:5), were very similar and shared 7/9 amino acids. When the in vivo homing specificity of these phage to the intracranial (i.c.) HIFko astrocytomas was tested, phage 36, hereafter referred to as CooP, showed nearly 20-fold homing to the tumor, while negligible homing to other organs including the liver, kidney, lung and the normal brain was detected (FIG. 1C). Homing of the phage 34 to tumor was modest, about 3-fold over the control phage (data not shown).

Tissue Localization of CooP

To confirm that the homing was mediated by the CooP peptide sequence and to study the tissue localization of the peptide more precisely the synthetic peptide was conjugated to fluorescein. FITC-CooP (100 µM, 100 µl/animal) was injected into the tail vein of i.c HIFko astrocytoma-bearing mice and allowed it to circulate for 60 minutes. The peptide accumulated in the tumor islets in the brain (data not shown). Adjacent tissue sections were stained for the presence of the SV40 large T antigen to visualize the tumor cells (data not shown). The CooP peptide was not detected in the surrounding histologically normal brain or other tissues examined (data not shown). Some peptide-derived fluorescence was observed in the kidneys and the choroid plexus, a cerebrospinal fluid secreting epithelial structure located in brain ventricles. Since a control peptide (E3) (Porkka et al., *Proc Natl Acad Sci USA.*, 99:7444-7449 (2002), the previously reported tumor-homing peptides F3 (Porkka et al., 2002), and LyP-1 (Laakkonen et al., *Nat Med.*, 8:751-755 (2002)) used as controls produced a similar fluorescent pattern at these sites (data not shown), the signals in the kidney and the choroid plexus were most likely produced by non-specific peptide or fluorescein uptake.

Tumor-Type Specificity of CooP

To assess tumor-type specificity of the CooP peptide, its homing to other types of brain tumors was tested. The CooP peptide homed efficiently to the intracranial U87MG human glioma xenografts (data not shown), and to a lesser yet detectable extent to the rat $BT_4C$ glioma xenografts (data not shown) after an intravenous injection. No CooP peptide was detected in the orthotopic MDA-MB-231 human breast cancer xenografts (FIG. 2F). Interestingly, the CooP peptide did not home to tumors established from the HIFko cells when they were implanted subcutaneously (data not shown). In addition, CooP peptide did not home to astrocytomas arising from same cells than HIFko tumors but overexpressing VEGF that contain massive network of angiogenic blood vessels (data not shown).

Mammary-derived growth inhibitor is the putative receptor for the CooP peptide. Due to its very specific homing the CooP peptide should bind to a receptor(s)/binding partner(s) on the target tissue.

Identification of a Receptor for CooP

Figure 2A:
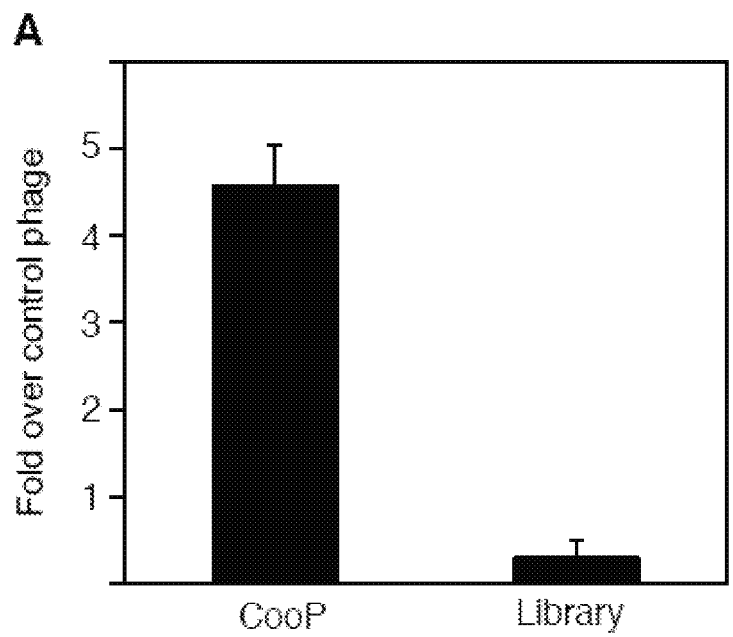
FIGS. 2A and 2B show the effect of MDGI expression on the binding of the CooP phage. U2OS cells were transfected with the MDGI encoding pcDNA3-9E10 plasmid.
Figure 2B:
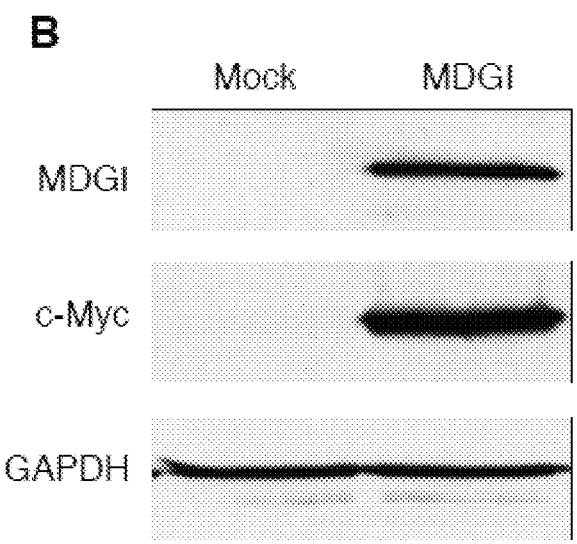
Figure 4:
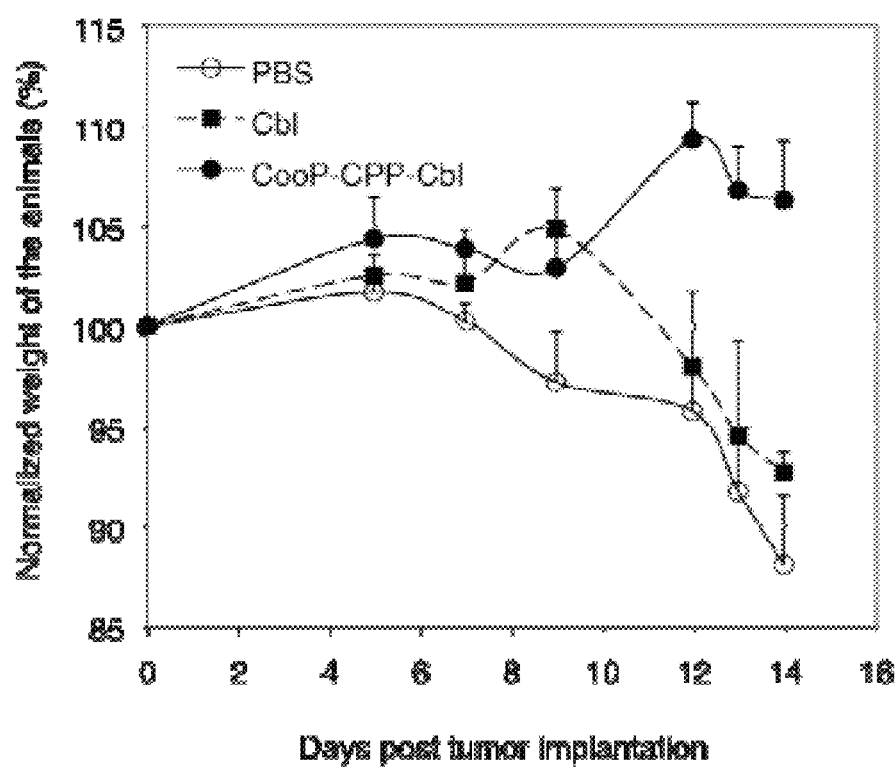
FIG. 4 is a graph showing weight gain in tumor bearing immunocompromised (Balb/c nu/nu) mice, treated with saline (PBS), free chlorambusil (Cbl), and targeted drug (chlorambusil conjugated to CooP peptide; CooP—CPP-Cbl, 5 mg/kg). The graph shows the normalized weight of each group of the animals. Weight on day 0 (the day of implantation) was set to 100%.

To identify a receptor for the CooP peptide, a yeast-two-hybrid screen, was used (Fields and Song, 1989). The peptide sequence was introduced into the bait plasmid and co-transformed to bacteria with the target plasmids encoding a murine embryonic (E12.5) cDNA library. An embryonic library was selected since the CooP peptide did not home to the normal brain and many embryonic proteins become upregulated in tumor tissues but are not present in the normal adult tissues (e.g. c-Myc, the EDB domain of oncofetal fibronectin (Carnemolla et al., J Cell Biol 108, 1139-1148 (1989), Castellani et al., Int J Cancer 59, 612-618 (1994), Kaczmarek et al., Int J Cancer 59, 11-16 (1994), Zardi et al., EMBO J 6, 2337-2342 (1987)) and the large isoform of tenascin C (Borsi et al., Int J Cancer 52, 688-692 (1992), Carnemolla et al., Eur J Biochem 205, 561-567 (1992)). The yeast-two-hybrid screen yielded ten in-frame hits, which were used for sequence identification from the BLAST database. These cDNAs represented four different proteins: (i) a eukaryotic translational initiation factor (Eif3s7); (ii) a neural peptidase (Cpe); (iii) a mammary-derived growth inhibitor (MDGI); and (iv) an EST. Three of the hits represented two different cDNAs for the MDGI. MDGI expression in the transiently transfected U2OS cells increased the binding of CooP displaying phage 10-fold compared to the original library (FIG. 2A). MDGI expression in transfected cells was confirmed by Western blot analyses (FIG. 2B). After this initial validation MDGI, also known as the fatty-acid binding protein 3 (Fabp3) or the heart fatty acid-binding protein (H-FABP), was further investigated as a potential receptor for the CooP peptide.

To act as a receptor molecule for the CooP homing peptide, MDGI should be expressed either by the tumor cells and/or tumor-associated stromal cells. First, the expression of MDGI in those tumors to which the CooP peptide homed was investigated. FITC-tagged CooP peptide was injected i.v. into the intracranial HIFko and U87MG tumor-bearing mice. Tumor sections were then studied for the presence of the peptide as well as for the MDGI expression using an antibody against MDGI. The MDGI protein was detected both in the U87MG and HIFko brain tumors. Furthermore, partial co-localization of the MGDI and the peptide was observed in the tumor tissue (data not shown). The homing pattern of the CooP peptide after systemic delivery varied in different i.c. tumors; in the HIFko tumor islets the peptide showed diffuse distribution throughout the islet (data not shown) while in the U87MG human glioma xenografts the peptide displayed a vessel-like homing pattern (data not shown). Importantly, MDGI was expressed in all tumors the CooP peptide homed to (i.c. HIFko, U87MG, and $BT_4C$ tumors; data not shown) and MDGI expression was absent in the tumors to which the CooP peptide did not home (i.c. VEGF-overexpressing tumor, orthotopic MDA-MD-231 breast cancer xenograft and subcutaneous HIFko tumor; data not shown).

CooP Homing to MDGI-Expressing Xenografts

To further validate the MDGI as a receptor for the CooP peptide, an MDGI expressing MDA-MB-231 tumor cell line was established and used to monitor whether the presence of MDGI would allow the CooP homing to the MDA-MB-231 tumors. The CooP peptide homed with high efficiency to all MDGI-expressing xenografts analyzed (data not shown) while only negligible amount of the peptide was detected in the parental MDA-MB-231 tumor (data not shown). Thus, the presence of MDGI in the tumor tissue increased substantially the homing of the CooP peptide to these tumors.

MDGI, being the cardiac isoform of the fatty-acid binding proteins is abundantly expressed in the muscle and heart, and to a lesser extent, in the brain (Zschiesche et al., *Histochem Cell Biol*, 103:147-156 (1995)). Therefore the MDGI expression in the U87MG brain tumor-bearing mice was studied. To visualize the blood vasculature these mice were perfused with FITC-lectin (from *Lycopercicon esculanta*). MDGI was expressed in the tumor (data not shown), muscle (data not shown) and heart (data not shown) but MDGI expression was not detected in the brain with the antibody and staining method used (data not shown). Interestingly, MDGI showed vasculature-associated expression only in the tumors (data not shown).

Circulating Anti-MDGI Antibody Localizes to Tumor-Associated Blood Vessels

The CooP peptide selectively homed to a subtype of brain tumors when expressed as a part of the phage capsid protein or when conjugated to a fluorescein label. This prompted us to investigate whether antibodies against MDGI, the potential binding partner of the peptide, would also accumulate in tumors. Furthermore, MDGI should be accessible via the circulation to act as a receptor for the systemically administered peptide. The anti-MDGI antibody was administered intravenously to the i.c. U87MG tumor-bearing mice. Histological analysis of tissues showed accumulation of the anti-MDGI antibody in the tumor-associated vasculature (data not shown) whereas blood vessels in other tissues such as muscle (data not shown), heart (data not shown), normal brain (data not shown), kidney, liver, and lung (data not shown) showed no detectable accumulation of the antibody. Goat IgG, which served as a control did not accumulate in tumor vasculature or in any other tissue examined (data not shown). Thus, in the tumor tissue MDGI is accessible via the blood circulation, and can therefore act as a receptor molecule for the intravenously administered homing peptide.

SPECT/CT Imaging of Brain Tumors

Figure 3A:
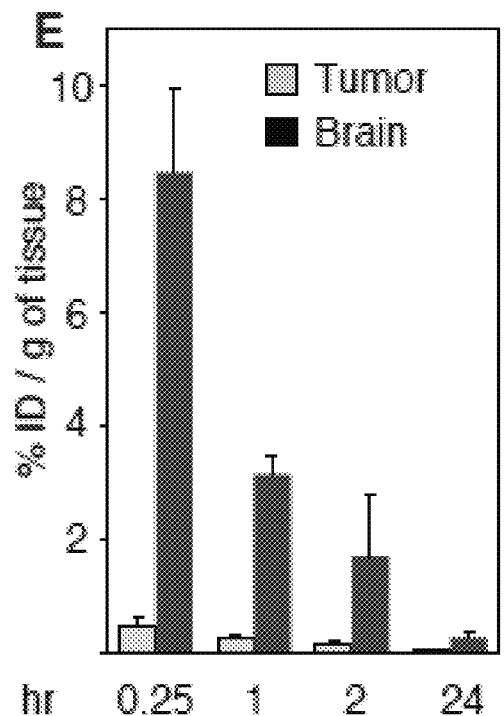
FIG. 3A shows CooP peptide accumulation (% ID $g^{-1}$±STD) in the tumor half and the healthy half of the brain of the same animal 0.25, 1, 2 and 24 hrs after intravenous administration of 5 MBq $^{111}$In-CooP.
Figure 3B:
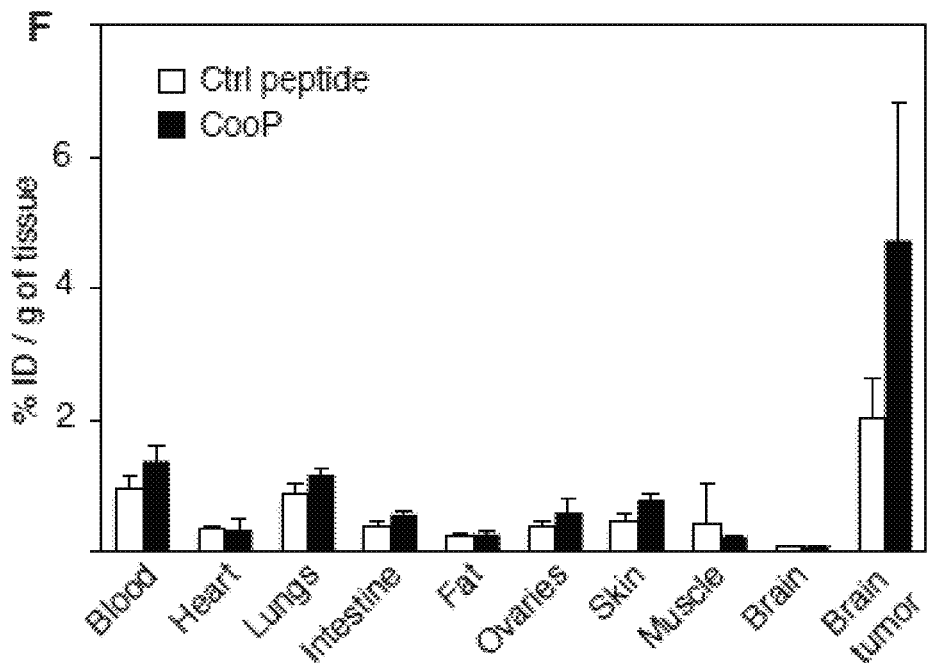
FIG. 3B shows biodistribution of the $^{111}$In-CooP and the $^{111}$In-labeled control peptide (% ID $g^{-1}$±STD) in different tissues at two hours after intravenous administration of the peptides.
Figure 3C:
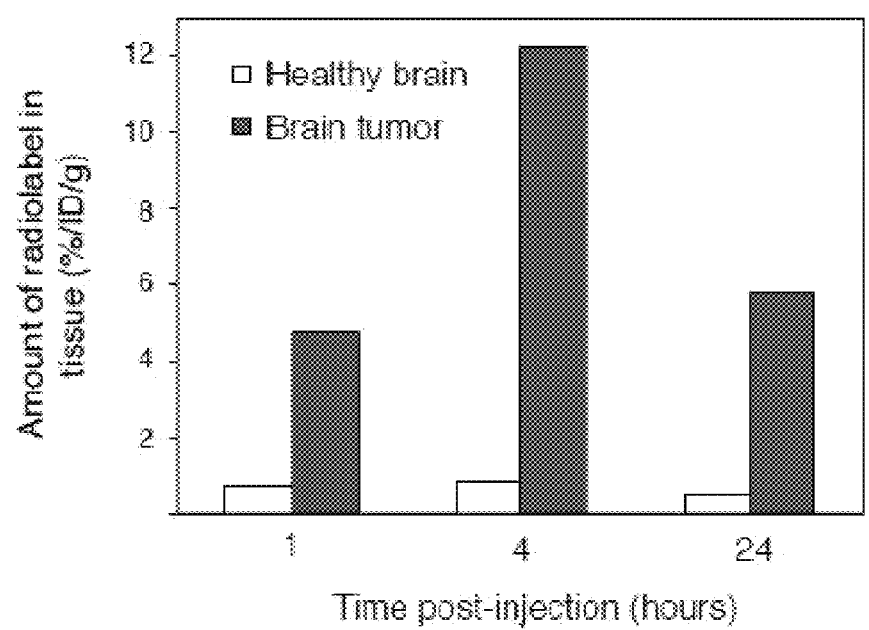
FIG. 3C shows accumulation of $^{111}$Indium-labeled anti-MDGI antibody in the brain tumor tissue following injection of anti-MDGI antibody (goat anti-MDGI, Santa Cruz Biotechnology) was injected into the tail vein of U87MG human glioma bearing mice and allowed to circulate for indicated times. The animals were sacrificed and the radioactivity was measured in the healthy half and brain tumor containing brain half of the same animal.

DTPA conjugated CooP-peptide was labeled with $^{111}$In and injected it (20 μg in 100 μl) intravenously into i.c. U87MG tumor-bearing mice. 2D images were collected from all animals up to 15-30 min post-injection. A 3D image was reconstructed 60 min, 120 min or 24 hrs post-injections. The plasma clearance of the peptide was rapid since most of the activity was excreted in the urine within the first 20 minutes (data not shown). Despite rapid clearance, uptake of $^{111}$In-CooP in the U87MG glioma was evident in ⅓ mice (5.41±0.07% ID/g$^{-1}$) at 60 min post-injection, and in ⅚ mice (2.43±0.85% ID g$^{-1}$) at 120 min post-injection (data not shown). The tumor-to-blood ratio increased from 1.38±0.38 at 60 min to 2.49±0.02 at 120 min resulting in improved tumor resolution and detection in SPECT. No accumulation of an $^{111}$In-labeled control peptide was present in the tumor tissue two hours post-injection (data not shown). Tumor site radioactivity was approximately 20-fold higher at 15 min post-injection and about 12-fold higher at two hours post-injection compared to the contralateral brain hemisphere, indicating marked CooP peptide accumulation in the malignant tissue (FIG. 3A). Importantly, only brain tumors showed increased accumulation of the CooP peptide compared to the control peptide at 2 hrs post-injection (FIG. 3B). Tumor site radioactivity was increased over healthy brain at all times measured (FIG. 3B).

MDGI Expression in Human Brain Tumors

The data shows that MDGI is the receptor molecule for the CooP peptide in the experimental brain tumors. MDGI expression in human brain tumors has not been reported earlier. The presence and localization of MDGI in clinical brain tumor samples was investigated by immunohistochemistry. First, a small panel of astrocyte-derived tumor samples from patients who had undergone craniotomy was analyzed (Table 1). Normal brain tissue (data not shown) and pilocytic astrocytomas (grade 1) did not express MDGI at detectable levels (data not shown). Interestingly, the majority of the grade 2 astrocytomas (60%) (data not shown) and 80% of anaplastic astrocytomas (data not shown) showed moderate levels of MDGI expression mostly in the vasculature and in the perivascular compartment. Of glioblastomas $^{17}$⁄$_{18}$ (94%) expressed very high levels of MDGI. The expression was concentrated on perinecrotic areas of the tumors (data not shown), i.e., all but one of the glioblastomas expressed very high levels of MDGI. The expression was concentrated on perivascular and perinecrotic areas of the tumors (data not shown). Vasculature-associated MDGI was also found in some glomeruloid- and slit-like vessels that are typical for the GBM (data not shown). Sixty-seven percent of ependymomas were moderately positive while medulloblastomas () showed no MDGI expression (data not shown).

Generally, less than 50% of grade 1 tumor types express MDGI, over 50% of grade 2, over 70% of grade 3, and over 90% of grade 4. MDGI expression in human brain tumors is presented in Table 1.

TABLE 1

MDGI Expression in Bain Tumors

| Tumor type | N | MDGI positive (%) | MDGI negative (%) |
|---|---|---|---|
| Pilosytic astrocytoma g1 | 5 | 0 (0) | 5 (100) |
| Astrocytoma g2 | 5 | 3 (60) | 2 (40) |
| Anasplastic astrocytoma g3 | 5 | 4 (80) | 1 (20) |
| Glioblastoma g4 | 18 | 17 (94) | 1 (6) |
| Medulloblastoma | 5 | 0 (0) | 5 (100) |
| Ependymoma | 3 | 2 (67) | 1 (33) |

A small array of human glioblastoma (n=46), clear cell kidney carcinomas (n=4), sarcomas (n=18), ovarian (n=16), pancreatic (10) and breast carcinoma (n=33) samples as well as testicular cancer (n=29), melanoma (n=11) and prostate carcinoma (n=4) samples, was also examined for the presence of MDGI expression. In this analysis 70% (32/46) of gliomas, 100% (4/4) of kidney carcinomas, 89% (16/18) of sarcomas, 88% (14/16) of ovarian carcinomas, 80% (8/10) of pancreatic carcinomas, 12% (4/33) of breast carcinomas, 86% (25/29) of testicular cancers, 64% (7/11) of melanomas and 50% (2/4) of prostate carcinomas were positive for the MDGI expression.

The data clearly demonstrate that MDGI is present in human brain tumors in a grade-dependent manner, and its expression positively correlates with the histological grade of the tumor.

The Role of MDGI Expression Levels on Tumor Progression and Metastasis

The levels of MDGI in the serum of MDGI-expressing orthotopic glioma and subcutaneous MDA-MB-231 breast carcinoma xenograft-bearing mice were compared to that of healthy animals using Western blot analyses. The MDGI-expressing xenograft bearing mice had considerable amounts of MDGI in the serum, whereas no MDGI was detected in the serum of healthy animals. This indicates that the serum or plasma levels of MDGI are useful as surrogate marker for brain tumor diagnosis and the efficacy of the therapy. Prominin (CD133) positive cells were isolated from the commercially available human glioma cell line U87MG and created a CD133-positive cell line. These cells should represent the glioma stem or initiating cells. When the CD133+ cells were implanted intracranially into mice and analyzed the amount of MDGI in their serum, elevated levels of MDGI in the serum were detected, compared to that of the parental U87MG tumor-bearing animals. This indicated that MDGI becomes upregulated in the glioma stem cells. Both the localization of MDGI in the brain tumor samples and its increased serum expression by glioma stem cell-derived tumor bearing mice indicates expression of MDGI by the glioma stem cells.

The human breast cancer xenografts derived from the MDA-MB-231 cells expressed MDGI at very low levels; therefore stable MDA-MB-231 cell lines expressing moderate or high levels of the MDGI protein were created. Xenograft tumors of these stable MDGI-MDA cells were established and their growth rate and metastatic potential compared to that of MDA-MB-231 xenografts. The data showed that tumors arising from cells expressing moderate levels of MDGI grew similarly to the MDA-MB-231 tumors while tumors generated from the high MDGI expressing cells grew well, initially, but then started to regress. Interestingly, differences in the metastatic spread between these tumors was also observed the MDA-MB-231 (low levels of MDGI) tumors metastasized only to the lymph nodes, whereas the MDGI moderate and high expressing clones metastasized frequently to the liver and brain indicating a functional role for MDGI in tumor metastasis.

To investigate the role of MDGI in brain tumor progression and invasion more thoroughly stable human U87MG glioma cells expressing MDGI-GFP (GFP=green fluorescent protein) using the lentiviral vectors were created. The MDGI-GFP expressing U87MG intracranial tumors showed invasive phenotype in contrast to the GFP expressing U87MG control tumors, which grew locally in the injection site, indicating a role for MDGI also in brain tumor invasion (data not shown). In order to study the invasion potential of MDGI expressing cells a collagen invasion assay was performed. In this assay tumor cells were seeded on top of an insert coated with collagen. The invasion of tumor cells into the collagen was monitored daily during the experiment. MDGI expressing MDA-MB-231 breast carcinoma cells invaded significantly more than the parental MDA-MB-231 cells (data not shown).

The data from these studies show that MDGI expressing brain tumors and breast carcinomas show increased invasion and metastatic capacity compared to the parental tumors in vivo. The data also showed increased invasive potential of MDGI expressing breast carcinoma cells in vitro. Accordingly, tumor invasion and metastasis can be reduced by reducing the MDGI expression. This can be performed for example by using the RNAi technology or possibly using antibodies against MDGI. ShRNA or SiRNA, being capable of specifically silencing MDGI expression, can be produced by methods well known to a person skilled in the art. Also antibodies recognizing MDGI can be used to reduce tumor invasion and metastasis.

Targeted Treatment Prolongs the Survival of the Brain Tumor Bearing Mice.

Tumor bearing immunocompromised (Balb/c nu/nu) mice treated with saline (PBS), free chlorambusil (Cbl) or targeted drug (chlorambusil conjugated to CooP peptide; CooP—CPP-Cbl, 5 mg/kg) showed marked differences in response to treatment as measured by the weight gain from the normalized weight at tumor cell implantation. The data shows that targeted treatment can prolong the survival of brain tumor bearing mice, which show a dramatic improvement in weight gain as when compared to mice treated with saline or free chlorambusil.

Discussion

The studies disclosed herein show that mammary-derived growth inhibitor (MDGI), also designated Fabp3 or H-FABP, the heart isoform of the fatty acid-binding proteins (FABPs), acts as a receptor for our peptide in the brain tumor tissue based on the following data. First, a yeast-2-hybrid screen using the peptide sequence as bait yielded three different MDGI cDNAs indicating that this protein binds to the CooP peptide. Second, MDGI expression was analogous with the homing of CooP. MDGI was expressed only in tumors the CooP peptide homed to. Accordingly, tumors the CooP peptide did not home to were negative for MDGI expression. Interestingly, the expression of MDGI and the homing of the peptide seemed to be dependent on the tumor microenvironment since the HIFko tumors in the subcutaneous space did not express the receptor and the peptide did not home to those tumors in contrast to the same tumors grown in the intracranial space. This is in line with the pre-existing data showing that the tumor microenvironment affects maturation of the vasculature and that the molecular composition of blood vessels at diverse locations is different (Madri et al., 1983, Janzer et al., 1987, Aird et al., 1997, Blouw et al. 2003). Third, the binding of the Coop peptide to the MDGI transfected cells compared to the non-selected peptide library was markedly higher in vitro, and MDGI overexpression dramatically increased the homing of the peptide to the tumor xenografts in vivo. Fourth, circulating antibodies against the MDGI accumulated only in the tumor tissue but were non-detectable in other tissues indicating MDGI to be adequately accessible through the circulation and exposed to intravenously injected ligands.

It is noteworthy that the MDGI was also expressed in heart and skeletal muscle as previously described (Zschiesche et al., *Histochem Cell Biol*, 103:147-156 (1995)). Low levels of MDGI were observed in the lining epithelia of brain ventricles and choroid plexus but importantly, vascular expression was restricted to the tumor tissue allowing the tumor specific homing of the peptide. Another example of tissue-specific vascular expression is the membrane dipeptidase (MDP), the receptor for the lung-homing peptide GFE-1. Vasculature-associated MDP in the lung microvasculature allows lung homing of the peptide. MDP is also expressed in the proximal tubules of the kidney but there it is not expressed in the vascular compartment and therefore inaccessible via vascular targeting (Rajotte et al., *Journal of Clinical Investigation*, 102:430-437 (1998); Rajotte and Ruoslahti, *Journal of Biological Chemistry*, 274:11593-11598 (1999)).

The FABPs are primarily intracellular proteins, although membrane-associated forms have also been reported (Glatz and van der Vusse, *rog Lipid Res*, 35:243-282 (1996)) that mediate the fatty acid and/or hydrophobic ligand uptake, transport and targeting in their respective tissues (Veerkamp, *Proc Nutr Soc.,* 54:23-37 (1995)). In cells transiently overexpressing the MDGI, a small fraction of the protein was detected on the surface although the majority of the protein localized to the cytoplasm. Interestingly, this extracellular fraction was greater in transformed murine astrocytes than in other cell types. The extracellular/cell surface localization of intracellular proteins is not an unusual phenomenon in tumors, and cell surface or plasma membrane localization has been reported previously for several cytoplasmic, nuclear and even mitochondrial proteins: grp78 (Arap et al., *Cancer Cell*, 6:275-284 (2004)), nucleolin (Christian et al., *J Cell Biol.,* 163:871-878 (2003)), annexin (Oh et al., *Nature*, 429:629-635 (2004)), heat-shock proteins 90 alpha, hsp70 and gp96 (Eustace and Jay, *Cell Cycle,* 3:1098-1100 (2004); Eustace et al., *Nat Cell Biol.,* 6:507-514 (2004); Melendez et al., 11:334-342 (2006), derlin (Melendez et al., 2006), and p32 (Fogal et al., *Cancer Res.,* 68:7210-7218 (2008)). The mechanism of the transport of these intracellular proteins remains to be solved.

The role of MDGI in tumor progression is somewhat controversial. MDGI appears to be the only FABP that affects cell proliferation and differentiation. This function might be separate from its ligand binding function since it can be mimicked by a C-terminal peptide of MGDI, which cannot bind fatty acids (Yang et al., J. Cell Biol. 127:1097-1109 (1995), Wang and Kurtz, Oncogene 19(20):2455-60 (2000), Storch and Corsico, Annu. Rev. Nutr. 28:73-95 (2008)). The region of the genome coding for the MDGI is often deleted in sporadic breast cancers and MDGI appears to be downregulated in breast cancer cell lines via hypermetylation (Huynh et al., *Cancer Res.,* 56:4865-4870 (1996), Nevo et al., *Clin Cancer Res.,* 15:6570-6581 (2009). MDGI inhibits cell growth in culture and reduces the tumorigenicity of the MCF-7 breast cancer cells (Huynh and Pollak, *In Vitro Cell Dev Biol Anim.,* 31:25-29 (1995)). In MDA-MB-231 breast cancer cells, MDGI expression appears to inhibit invasion and adhesion (Nevo et al. Oncogene 29(49):6452-63 (2010)). On the other hand ectopic expression of MDGI has been shown to render breast and lung cancer cells resistant to the anti-EGFR antibody, cetuximab (Nevo et al., *Clin Cancer Res.,* 15:6570-6581 (2009)). Our results from the histological analysis of a small breast carcinoma array are in agreement with the previous studies showing the downregulation of MDGI in breast carcinomas. On the contrary, in small cell lung cancer (SCLC) MDGI expression was significantly higher in the highly aggressive cells than in its less aggressive subtype (Zhang et al., J. Surg. Res. 93(1):108-19 (2000)). Also in gastric carcinoma MDGI expression is associated with tumor aggressiveness, progression, and poor patient survival (Hashimoto et al., *Pathobiology,* 71:267-273 (2004)). Our data shows that MDGI is expressed in human astrocytomas and glioblastomas in a grade-dependent manner but is undetectable in the normal brain tissue. Also the small glioblastoma array analysis showed that the majority of the glioblastomas (70%) expressed MDGI. This indicates upregulation of MDGI in glial cell derived malignant tumors. The mechanism of upregulation remains to be elucidated. Our study showing the upregulation of MDGI in aggressive brain tumors is in accordance with the results obtained in SCLC and gastric cancer, and suggests MDGI as a novel marker for malignant brain tumors.

The specificity of the CooP peptide homing was demonstrated when biodistribution of the radioactively labeled peptide was studied, using the SPECT/CT. $^{111}$In-CooP accumulated very specifically to the U87MG brain tumors whereas only background levels of the peptide-associated radioactivity were detected in the normal brain. In addition, no accumulation of the scrambled control peptide was detected in the tumor. This was even more striking when the radioactivity in the tumor containing half of the brain was compared to that of the healthy half of the brain in same animals. The U87MG intracranial xenografts stayed local in the right hemisphere where originally injected unlike the HIFko tumors. Therefore no tumor was detected in the left hemisphere of the same animals. Tumor half to healthy brain half ratio was up to 20:1 indicating outstanding accumulation of the peptide in the tumor tissue while the whole-body radioactivity remained minimal. To date, peptide-based imaging strategies have been "dominated" by the RGD-peptide or its derivatives targeting the αvβ3 integrins in the angiogenic vessels, and the somatostatin receptor specific peptide analogues "hitting" the neuroendocrine tumors (reviewed in Reubi and Maecke, 2008). Also a few other peptides selected by phage-display have been utilized in in vivo imaging of tumors (Deutscher et al., *Nucl Med Biol.*, 36:137-146 (2009); Kumar and Deutscher, *J Nucl Med.*, 49:796-803 (2008); Kumar et al., *Clin Cancer Res.*, 13:6070-6079 (2007). The "radioprofile" of $^{111}$In-CooP peptide provides a potential new lead for the improved imaging of brain tumors.

A subset of tumors, including low-grade astrocytomas, initially grows by co-opting existing blood vessels. Glioblastomas first regress the co-opted host vasculature before they initiate the growth of new blood vessels i.e. angiogenesis. Angiopoietin 2 (Ang-2) is upregulated in the co-opted blood vessels prior their regression and it is associated with the vascular regression in the absence of vascular endothelial growth factor (VEGF) expression (Holash et al., *Science*, 284:1994-1998 (1999), Holash et al., *Oncogene*, 18:5356-5362 (1999)). Interestingly, the CooP peptide homed to the infiltrative tumor islets harboring co-opted blood vessels of the low-grade murine astrocytoma model. Ang-2 is not upregulated in the co-opted vessels of this tumor model and no transition to the angiogenic vasculature has been observed (Blouw et al., 2003). Recently, several papers have reported increased invasiveness as a mechanism for brain tumors to adapt to anti-angiogenic therapies (di Tomaso et al. *Cancer Res* 71, 19-28 (2011), Kunkel et al., *Cancer Research*, 61:6624-6628 (2001); Leenders et al., *Clin Cancer Res.*, 10:6222-6230 (2004), Paez-Ribes et al. Cancer Cell 15, 220-231 (2009), Rubenstein et al., *Neoplasia*, 2:306-314 (2000)). As our peptide was originally isolated using an in vivo model for infiltrative brain tumor it can be useful as a drug-shuttle aside angiogenesis blockers to eradicate both the primary tumor and the emerging satellites in cases primary tumor cannot be operated or when tumor satellites are left behind after the surgical resection of the primary tumor. The limited expression of MDGI in a subset of tumor endothelium makes it a promising target for peptide or antibody-mediated tumor therapy.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Those skilled in the art will recognize, or be able to ascertain using no more than routine experimentation, many equivalents to the specific embodiments of the method and compositions described herein. Such equivalents are intended to be encompassed by the following claims.

We claim:

1. A method for targeted therapy in a patient with brain cancer comprising administering to a patient in need of such therapy an effective amount of a pharmaceutical composition comprising anti-mammary-derived growth inhibitor (MDGI) antibody and a cancer chemotherapeutic agent.

2. The method according to claim 1 further comprising combining the targeted therapy with a cancer therapy, wherein the cancer therapy cancer is radiation therapy, surgery, siRNA or shRNA for MDGI to inhibit MDGI expression or function in the brain of the patient, or combinations thereof.

3. The method of claim 1, wherein the chemotherapeutic agent is selected from the group consisting of a taxane, an antracyclin, an alkylating agent, a vinca alkaloid, an antimetabolite, a platinum agent, a steroid, an antibiotic, a selective estrogen receptor modulator and an antibody cancer therapeutic agent.

4. The method of claim 3, wherein the cancer therapeutic agent is selected from the group consisting of docetaxel, doxorubicin, cisplatin, carboplatin, methotrexate, adriamycin, and trastuzumab.

5. The method of claim 2, wherein the composition further comprises a peptide comprising SEQ ID NO:5 or a variant thereof.

6. The method of claim 5, wherein the anti-MDGI antibody is conjugated to SEQ ID NO:5 or a variant thereof.

7. The method of claim 2, wherein the composition is administered after surgical removal of the brain tumor.

* * * * *